US011059905B2

(12) United States Patent
Boross et al.

(10) Patent No.: US 11,059,905 B2
(45) Date of Patent: Jul. 13, 2021

(54) MONOCLONAL ANTIBODIES AGAINST THE ACTIVE SITE OF FACTOR XI AND USES THEREOF

(71) Applicant: Prothix B.V., Leiden (NL)

(72) Inventors: Péter Boross, Utrecht (NL); Cafer Yildiz, Arnhem (NL); Cornelis Erik Hack, Diemen (NL)

(73) Assignee: Prothix B.V., Leiden (NL)

( * ) Notice: Subject to any disclaimer, the term of this patent is extended or adjusted under 35 U.S.C. 154(b) by 240 days.

(21) Appl. No.: 16/087,686

(22) PCT Filed: Mar. 23, 2017

(86) PCT No.: PCT/EP2017/056924
§ 371 (c)(1),
(2) Date: Sep. 24, 2018

(87) PCT Pub. No.: WO2017/162791
PCT Pub. Date: Sep. 28, 2017

(65) Prior Publication Data
US 2019/0106509 A1    Apr. 11, 2019

(30) Foreign Application Priority Data
Mar. 23, 2016 (NL) ...................................... 2016477

(51) Int. Cl.
| C07K 16/36 | (2006.01) |
| A61P 7/02 | (2006.01) |
| C12N 15/62 | (2006.01) |
| A61K 39/00 | (2006.01) |

(52) U.S. Cl.
CPC .............. *C07K 16/36* (2013.01); *A61P 7/02* (2018.01); *C12N 15/62* (2013.01); *A61K 2039/505* (2013.01); *C07K 2317/24* (2013.01); *C07K 2317/71* (2013.01); *C07K 2317/76* (2013.01); *C07K 2317/92* (2013.01)

(58) Field of Classification Search
None
See application file for complete search history.

(56) References Cited

U.S. PATENT DOCUMENTS 8,236,316 B2 * 8/2012 Gruber ...................... A61P 9/10
424/145.1
8,568,724 B2 * 10/2013 Hack ...................... C07K 16/36
424/145.1

FOREIGN PATENT DOCUMENTS

| WO | WO2009/154461 | 12/2009 |
| WO | WO2010/080623 | 7/2010 |
| WO | WO2013/167669 | 11/2013 |
| WO | WO-2013167669 A1 * | 11/2013 | ................ A61P 7/02 |
| WO | WO2016/207858 | 12/2016 |
| WO | WO-2016207858 A1 * | 12/2016 | ............. C07K 16/40 |

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Badreldin et al., Interact Cardiovasc Thorac Surg. May 2010;10(5):766-9. Epub Feb. 12, 2010.*
Sinha et al., J Biol Chem. Sep. 5, 1985;260(19): 10714-9.*
A. Matafonov et al: Evidence for factor IX-independent roles for factor XIa in blood coagulation, Journal of Thrombosis and Haemostasis, vol. 11, No. 12, (Dec. 1, 2013), pp. 2118-2127.
Linkins, Lori-Ann; Choi, Peter T.; Douketis, James D. Clinical impact of bleeding in patients taking oral anticoagulant therapy for venous thromboembolism: a meta-analysis. Annals of internal medicine, 2003, 139.11: 893-900.
Peyvandi, Flora; Lak, Manijeh; Mannucci, Pier Mannuccio. Factor XI deficiency in Iranians: its clinical manifestations in comparison with those of classic hemophilia. Haematologica, 2002, 87.5: 512-514.
Castaman, G., et al. The spectrum of factor XI deficiency in Italy. Haemophilia, 2014, 20.1: 106-113.
Minnema, Monique C., et al. Enhancement of rabbit jugular vein thrombolysis by neutralization of factor XI. In vivo evidence for a role of factor XI as an anti-fibrinolytic factor. The Journal of clinical investigation, 1998, 101.1: 10-14.
Gruber, András; Hanson, Stephen R. Factor XI—dependence of surface-and tissue factor-initiated thrombus propagation in primates. Blood, 2003, 102.3: 953-955.
Tucker, Erik I., et al. Prevention of vascular graft occlusion and thrombus-associated thrombin generation by inhibition of factor XI. Blood, 2009, 113.4: 936-944.
Takahashi, Misaki, et al. Inhibition of factor XI reduces thrombus formation in rabbit jugular vein under endothelial denudation and/or blood stasis. Thrombosis research, 2010, 125.5: 464-470.
Van Montfoort, Maurits L., et al. Two novel inhibitory anti-human factor XI antibodies prevent cessation of blood flow in a murine venous thrombosis model. Thromb Haemost, 2013, 110.5: 1065-1073.

(Continued)

*Primary Examiner* — Michael Szperka
(74) *Attorney, Agent, or Firm* — N.V. Nederlandsch Octrooibureau; Tamara C. Stegmann; Catherine A. Shultz

(57) ABSTRACT

The present invention provides novel anti-factor XI (FXI) antibodies and compositions comprising such antibodies. The anti-FXI antibodies of the invention specifically bind to the active center of FXI and inhibit the functional activity of FXI. The invention further provides humanized versions of the anti-FXI antibodies that are useful in the prevention and treatment of conditions in which pathological thrombus formation or thrombo-embolism are involved. The invention further provides nucleic acid molecules encoding the anti-FXI antibodies, cells expressing the anti-FXI antibodies and methods for producing the anti-FXI antibodies.

14 Claims, 12 Drawing Sheets
Specification includes a Sequence Listing.

(56) References Cited

OTHER PUBLICATIONS

Zhang, Hong, et al. Inhibition of the intrinsic coagulation pathway factor XI by antisense oligonucleotides: a novel antithrombotic strategy with lowered bleeding risk. Blood, 2010, blood-2010-04-277798.
Younis, Husam S., et al. Antisense inhibition of coagulation factor XI prolongs APTT without increased bleeding risk in cynomolgus monkeys. Blood, 2012, blood-2011-10-387134.
Büller, Harry R., et al. Factor XI antisense oligonucleotide for prevention of venous thrombosis. New England Journal of Medicine, 2015, 372.3: 232-240.
Sinha, Dipali, et al. Functional characterization of human blood coagulation factor XIa using hybridoma antibodies. Journal of Biological Chemistry, 1985, 260.19: 10714-10719.
Akiyama, Hideki, et al. Mechanism of activation of coagulation factor XI by factor XIIa studied with monoclonal antibodies. The Journal of clinical investigation, 1986, 78.6: 1631-1637.
Sinha, Dipali, et al. Macromolecular substrate-binding exosites on both the heavy and light chains of factor XIa mediate the formation of the Michaelis complex required for factor IX-activation. Biochemistry, 2007, 46.34: 9830-9839.
van Montfoort, M. L. (2014). Factor XI as target for antithrombotic therapy. (Phd Thesis).

* cited by examiner

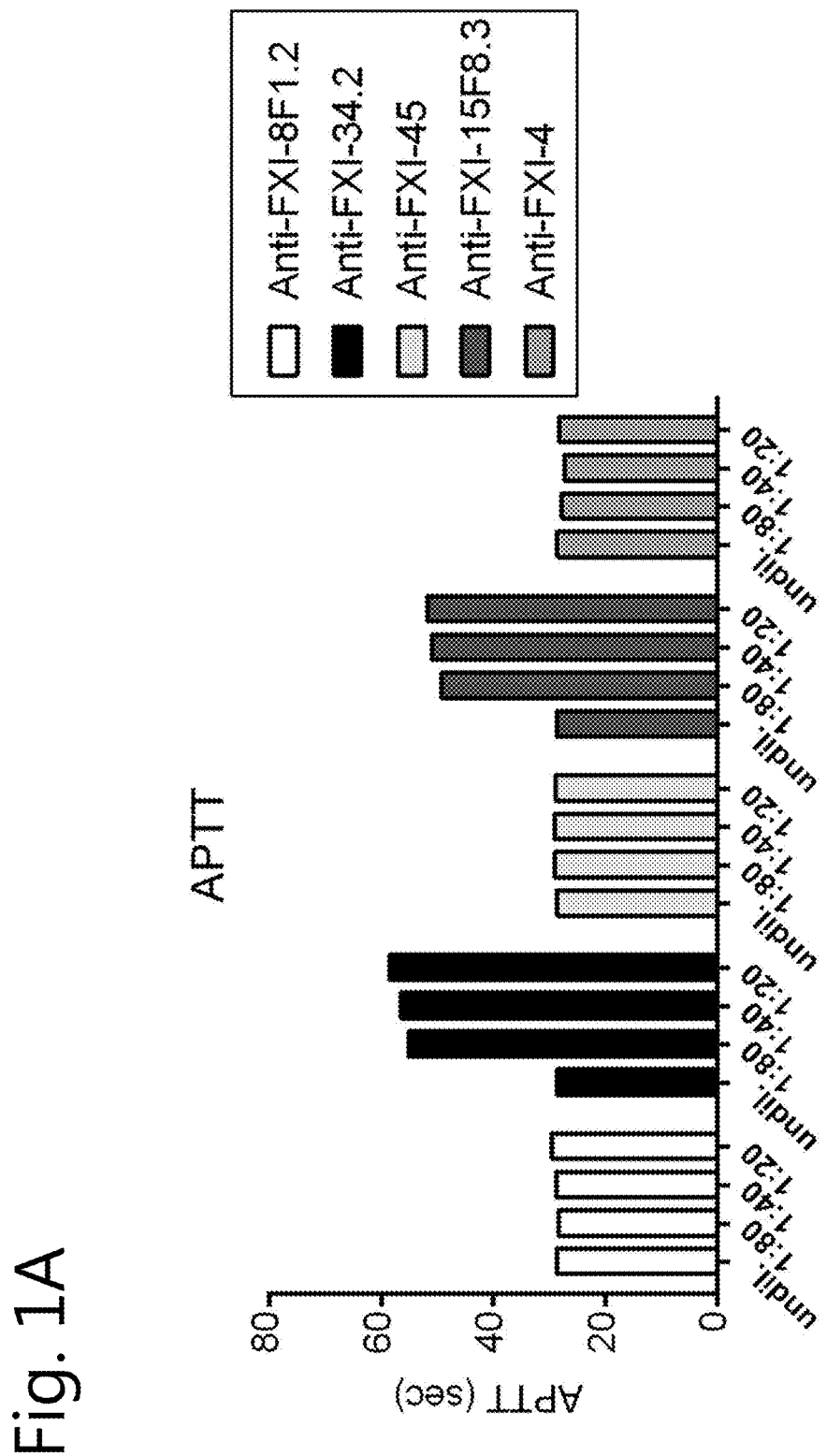

SEQUENCE LISTING

```
<160> NUMBER OF SEQ ID NOS: 28

<210> SEQ ID NO 1
<211> LENGTH: 117
<212> TYPE: PRT
<213> ORGANISM: Mus musculus

<400> SEQUENCE: 1

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Lys Gln Arg His Gly Gln Gly Leu Glu Trp Ile
        35                  40                  45

Gly Asn Ile Tyr Pro Asp Ser Asp Ser Thr Asn Tyr Asp Glu Lys Phe
    50                  55                  60
```

```
Arg Thr Lys Ala Thr Leu Thr Ala Asp Thr Ser Ser Thr Ala Tyr
 65                  70                  75                  80

Met His Leu Ser Ser Leu Thr Ser Glu Asp Ser Ala Val Tyr Tyr Cys
                 85                  90                  95

Thr Arg Met Gly Phe Tyr Ala Met Asp Tyr Trp Gly Gln Gly Thr Ser
            100                 105                 110

Val Thr Val Ser Ser
            115

<210> SEQ ID NO 2
<211> LENGTH: 108
<212> TYPE: PRT
<213> ORGANISM: Mus musculus

<400> SEQUENCE: 2

Asn Ile Val Met Thr Gln Ser Pro Lys Ser Met Ser Met Ser Val Gly
  1               5                  10                  15

Glu Arg Val Thr Leu Ser Cys Lys Ala Ser Glu Asn Val Val Thr Tyr
                 20                  25                  30

Val Ser Trp Phe Gln His Lys Pro Glu Gln Ser Pro Lys Leu Leu Ile
             35                  40                  45

Tyr Gly Ala Ser Asn Arg Tyr Thr Gly Val Pro Asp Arg Phe Thr Gly
 50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Ser Tyr Ser Tyr Pro Leu
                 85                  90                  95

Thr Phe Gly Ala Gly Thr Lys Leu Glu Leu Lys Arg
            100                 105

<210> SEQ ID NO 3
<211> LENGTH: 5
<212> TYPE: PRT
<213> ORGANISM: Mus musculus

<400> SEQUENCE: 3

Arg Tyr Trp Met His
  1               5

<210> SEQ ID NO 4
<211> LENGTH: 17
<212> TYPE: PRT
<213> ORGANISM: Mus musculus

<400> SEQUENCE: 4

Asn Ile Tyr Pro Asp Ser Asp Ser Thr Asn Tyr Asp Glu Lys Phe Arg
  1               5                  10                  15

Thr

<210> SEQ ID NO 5
<211> LENGTH: 8
<212> TYPE: PRT
<213> ORGANISM: Mus musculus

<400> SEQUENCE: 5

Met Gly Phe Tyr Ala Met Asp Tyr
  1               5

<210> SEQ ID NO 6
<211> LENGTH: 11
```

```
<212> TYPE: PRT
<213> ORGANISM: Mus musculus

<400> SEQUENCE: 6

Lys Ala Ser Glu Asn Val Val Thr Tyr Val Ser
1               5                   10

<210> SEQ ID NO 7
<211> LENGTH: 7
<212> TYPE: PRT
<213> ORGANISM: Mus musculus

<400> SEQUENCE: 7

Gly Ala Ser Asn Arg Tyr Thr
1               5

<210> SEQ ID NO 8
<211> LENGTH: 9
<212> TYPE: PRT
<213> ORGANISM: Mus musculus

<400> SEQUENCE: 8

Gly Gln Ser Tyr Ser Tyr Pro Leu Thr
1               5

<210> SEQ ID NO 9
<211> LENGTH: 26
<212> TYPE: DNA
<213> ORGANISM: Artificial
<220> FEATURE:
<223> OTHER INFORMATION: Heavy chain sense primer

<400> SEQUENCE: 9
atggratgga gckgggtctt tmtctt                                          26

<210> SEQ ID NO 10
<211> LENGTH: 21
<212> TYPE: DNA
<213> ORGANISM: Artificial
<220> FEATURE:
<223> OTHER INFORMATION: Heavy chain antisense primer

<400> SEQUENCE: 10
cagtggatag acagatgggg g                                               21

<210> SEQ ID NO 11
<211> LENGTH: 24
<212> TYPE: DNA
<213> ORGANISM: Artificial
<220> FEATURE:
<223> OTHER INFORMATION: Light chain sense primer

<400> SEQUENCE: 11
atgggcwtca aagatggagt caca                                            24

<210> SEQ ID NO 12
<211> LENGTH: 20
<212> TYPE: DNA
<213> ORGANISM: Artificial
<220> FEATURE:
<223> OTHER INFORMATION: Light chain antisense primer

<400> SEQUENCE: 12
actggatggt gggaagatgg                                                 20
```

<210> SEQ ID NO 13
<211> LENGTH: 117
<212> TYPE: PRT
<213> ORGANISM: Artificial
<220> FEATURE:
<223> OTHER INFORMATION: 34.2 mAb humanized heavy chain variable domain Variant 1

<400> SEQUENCE: 13

Gln Val Gln Leu Val Gln Ser Gly Ser Glu Leu Lys Lys Pro Gly Ala
1               5                   10                  15

Ser Val Lys Leu Ser Cys Lys Ala Ser Gly Tyr Thr Phe Thr Arg Tyr
                20                  25                  30

Trp Met His Trp Val Lys Gln Ala His Gly Gln Gly Leu Glu Trp Ile
            35                  40                  45

Gly Asn Ile Tyr Pro Asp Ser Asp Ser Thr Asn Tyr Asp Glu Lys Phe
        50                  55                  60

Arg Thr Arg Ala Thr Leu Thr Ala Asp Thr Ser Thr Ser Thr Ala Tyr
65                  70                  75                  80

Met His Leu Ser Ser Leu Thr Ser Glu Asp Ser Ala Val Tyr Tyr Cys
                85                  90                  95

Thr Arg Met Gly Phe Tyr Ala Met Asp Tyr Trp Gly Gln Gly Thr Ser
            100                 105                 110

Val Thr Val Ser Ser
        115

<210> SEQ ID NO 14
<211> LENGTH: 117
<212> TYPE: PRT
<213> ORGANISM: Artificial
<220> FEATURE:
<223> OTHER INFORMATION: 34.2 mAb humanized heavy chain variable domain Variant 2

<400> SEQUENCE: 14

Gln Val Gln Leu Val Gln Ser Gly Ser Glu Leu Lys Lys Pro Gly Ala
1               5                   10                  15

Ser Val Lys Leu Ser Cys Lys Ala Ser Gly Tyr Thr Phe Thr Arg Tyr
                20                  25                  30

Trp Met His Trp Val Lys Gln Ala Pro Gly Gln Gly Leu Glu Trp Ile
            35                  40                  45

Gly Asn Ile Tyr Pro Asp Ser Asp Ser Thr Asn Tyr Asp Glu Lys Phe
        50                  55                  60

Arg Thr Arg Ala Thr Leu Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Met Gly Phe Tyr Ala Met Asp Tyr Trp Gly Gln Gly Thr Thr
            100                 105                 110

Val Thr Val Ser Ser
        115

<210> SEQ ID NO 15
<211> LENGTH: 117
<212> TYPE: PRT
<213> ORGANISM: Artificial
<220> FEATURE:
<223> OTHER INFORMATION: 34.2 mAb humanized heavy chain variable domain Variant 3

<400> SEQUENCE: 15

Gln Val Gln Leu Val Gln Ser Gly Ser Glu Leu Lys Lys Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Arg Gln Ala Pro Gly Gln Gly Leu Glu Trp Ile
        35                  40                  45

Gly Asn Ile Tyr Pro Asp Ser Asp Ser Thr Asn Tyr Asp Glu Lys Phe
    50                  55                  60

Arg Thr Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Met Gly Phe Tyr Ala Met Asp Tyr Trp Gly Gln Gly Thr Thr
            100                 105                 110

Val Thr Val Ser Ser
        115

<210> SEQ ID NO 16
<211> LENGTH: 117
<212> TYPE: PRT
<213> ORGANISM: Artificial
<220> FEATURE:
<223> OTHER INFORMATION: 34.2 mAb humanized heavy chain variable domain
      Variant 4

<400> SEQUENCE: 16

Gln Val Gln Leu Val Gln Ser Gly Ser Glu Leu Lys Lys Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Arg Gln Ala Pro Gly Gln Gly Leu Glu Trp Ile
        35                  40                  45

Gly Asn Ile Tyr Pro Asp Ser Asp Ser Thr Asn Tyr Asp Glu Lys Phe
    50                  55                  60

Arg Thr Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Met Gly Phe Tyr Ala Met Asp Tyr Trp Gly Gln Gly Thr Thr
            100                 105                 110

Val Thr Val Ser Ser
        115

<210> SEQ ID NO 17
<211> LENGTH: 108
<212> TYPE: PRT
<213> ORGANISM: Artificial
<220> FEATURE:
<223> OTHER INFORMATION: 34.2 mAb humanized light chain variable domain
      Variant 1

<400> SEQUENCE: 17

Asn Ile Val Met Thr Gln Ser Pro Ser Ser Leu Ser Ala Ser Val Gly
1               5                   10                  15

Asp Arg Val Thr Ile Thr Cys Lys Ala Ser Glu Asn Val Val Thr Tyr
            20                  25                  30

Val Ser Trp Phe Gln Gln Lys Pro Gly Gln Ala Pro Lys Leu Leu Ile
        35                  40                  45

Tyr Gly Ala Ser Asn Arg Tyr Thr Gly Val Pro Asp Arg Phe Thr Gly
            50                  55                  60

Ser Gly Ser Ala Thr Asp Phe Thr Leu Thr Ile Ser Ser Leu Gln Ala
 65                  70                  75                  80

Glu Asp Val Ala Asp Tyr His Cys Gly Gln Ser Tyr Ser Tyr Pro Leu
                85                  90                  95

Thr Phe Gly Gln Gly Thr Lys Leu Glu Ile Lys Arg
                100                 105

<210> SEQ ID NO 18
<211> LENGTH: 108
<212> TYPE: PRT
<213> ORGANISM: Artificial
<220> FEATURE:
<223> OTHER INFORMATION: 34.2 mAb humanized light chain variable domain
      Variant 2

<400> SEQUENCE: 18

Asn Ile Val Met Thr Gln Ser Pro Ser Ser Leu Ser Ala Ser Val Gly
 1               5                  10                  15

Asp Arg Val Thr Ile Thr Cys Lys Ala Ser Glu Asn Val Val Thr Tyr
                20                  25                  30

Val Ser Trp Phe Gln Gln Lys Pro Gly Gln Ala Pro Lys Leu Leu Ile
            35                  40                  45

Tyr Gly Ala Ser Asn Arg Tyr Thr Gly Val Pro Asp Arg Phe Ser Gly
        50                  55                  60

Ser Gly Ser Ala Thr Asp Phe Thr Leu Thr Ile Ser Ser Leu Gln Ala
 65                  70                  75                  80

Glu Asp Val Ala Asp Tyr His Cys Gly Gln Ser Tyr Ser Tyr Pro Leu
                85                  90                  95

Thr Phe Gly Gln Gly Thr Lys Leu Glu Ile Lys Arg
                100                 105

<210> SEQ ID NO 19
<211> LENGTH: 108
<212> TYPE: PRT
<213> ORGANISM: Artificial
<220> FEATURE:
<223> OTHER INFORMATION: 34.2 mAb humanized light chain variable domain
      Variant 3

<400> SEQUENCE: 19

Asp Ile Val Met Thr Gln Ser Pro Ser Ser Leu Ser Ala Ser Val Gly
 1               5                  10                  15

Asp Arg Val Thr Ile Thr Cys Lys Ala Ser Glu Asn Val Val Thr Tyr
                20                  25                  30

Val Ser Trp Phe Gln Gln Lys Pro Gly Gln Ala Pro Lys Leu Leu Ile
            35                  40                  45

Tyr Gly Ala Ser Asn Arg Tyr Thr Gly Val Pro Asp Arg Phe Ser Gly
        50                  55                  60

Ser Gly Ser Gly Thr Asp Phe Thr Leu Thr Ile Ser Ser Leu Gln Ala
 65                  70                  75                  80

Glu Asp Val Ala Asp Tyr His Cys Gly Gln Ser Tyr Ser Tyr Pro Leu
                85                  90                  95

Thr Phe Gly Gln Gly Thr Lys Leu Glu Ile Lys Arg
                100                 105

<210> SEQ ID NO 20

<211> LENGTH: 108
<212> TYPE: PRT
<213> ORGANISM: Artificial
<220> FEATURE:
<223> OTHER INFORMATION: 34.2 mAb humanized light chain variable domain
      Variant 4

<400> SEQUENCE: 20

Asp Ile Val Met Thr Gln Ser Pro Ser Ser Leu Ser Ala Ser Val Gly
1               5                   10                  15

Asp Arg Val Thr Ile Thr Cys Lys Ala Ser Glu Asn Val Val Thr Tyr
            20                  25                  30

Val Ser Trp Phe Gln Gln Lys Pro Gly Gln Ala Pro Lys Leu Leu Ile
        35                  40                  45

Tyr Gly Ala Ser Asn Arg Tyr Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Thr Tyr His Cys Gly Gln Ser Tyr Ser Tyr Pro Leu
                85                  90                  95

Thr Phe Gly Gln Gly Thr Lys Leu Glu Ile Lys Arg
            100                 105

<210> SEQ ID NO 21
<211> LENGTH: 351
<212> TYPE: DNA
<213> ORGANISM: Artificial
<220> FEATURE:
<223> OTHER INFORMATION: nt sequence encoding humanized heavy chain
      variable domain variant 1

<400> SEQUENCE: 21
caggtgcagc tggtgcagtc tgggtctgag ctgaagaagc ctggagcttc agtgaagctc      60
tcctgcaagg cttctggata caccttcacc agatactgga tgcactgggt gaagcaggcc     120
catggacaag gcttgagtg gattggaaat atctatcctg atagtgatag tactaactac      180
gatgagaagt tcaggaccag agccaccctg accgcagaca catccacaag cacagcctac     240
atgcacctga gcagcctgac atctgaggac tctgccgtgt attactgtac aagaatgggt     300
ttctacgcta tggactactg gggccaaggg accagcgtca ccgtctcctc a              351

<210> SEQ ID NO 22
<211> LENGTH: 351
<212> TYPE: DNA
<213> ORGANISM: Artificial
<220> FEATURE:
<223> OTHER INFORMATION: nt sequence encoding humanized heavy chain
      variable domain variant 2

<400> SEQUENCE: 22
caggtgcagc tggtgcagtc tgggtctgag ctgaagaagc ctggagcttc agtgaagctc      60
tcctgcaagg cttctggata caccttcacc agatactgga tgcactgggt gaagcaggcc     120
cctggacaag gcttgagtg gattggaaat atctatcctg atagtgatag tactaactac      180
gatgagaagt tcaggaccag agccaccctg accgcagaca catccacaag cacagcctac     240
atggagctga gcagcctgag atctgaggac acggccgtgt attactgtac aagaatgggt     300
ttctacgcta tggactactg gggccaaggg accacggtca ccgtctcctc a              351

<210> SEQ ID NO 23
<211> LENGTH: 351

```
<212> TYPE: DNA
<213> ORGANISM: Artificial
<220> FEATURE:
<223> OTHER INFORMATION: nt sequence encoding humanized heavy chain
      variable domain variant 3

<400> SEQUENCE: 23
caggtgcagc tggtgcagtc tgggtctgag ctgaagaagc ctggagcttc agtgaagctc      60
tcctgcaagg cttctggata caccttcacc agatactgga tgcactgggt gcgccaggcc    120
cctggacaag ggcttgagtg gattggaaat atctatcctg atagtgatag tactaactac    180
gatgagaagt tcaggaccag agtcaccctg accgcagaca catccacaag cacagcctac    240
atggagctga gcagcctgag atctgaggac acggccgtgt attactgtac aagaatgggt    300
ttctacgcta tggactactg gggccaaggg accacggtca ccgtctcctc a              351

<210> SEQ ID NO 24
<211> LENGTH: 351
<212> TYPE: DNA
<213> ORGANISM: Artificial
<220> FEATURE:
<223> OTHER INFORMATION: nt sequence encoding humanized heavy chain
      variable domain variant 4

<400> SEQUENCE: 24
caggtgcagc tggtgcagtc tgggtctgag ctgaagaagc ctggagcttc agtgaaggtc      60
tcctgcaagg cttctggata caccttcacc agatactgga tgcactgggt gcgccaggcc    120
cctggacaag ggcttgagtg gattggaaat atctatcctg atagtgatag tactaactac    180
gatgagaagt tcaggaccag agtcaccatc accgcagaca catccacaag cacagcctac    240
atggagctga gcagcctgag atctgaggac acggccgtgt attactgtac aagaatgggt    300
ttctacgcta tggactactg gggccaaggg accacggtca ccgtctcctc a              351

<210> SEQ ID NO 25
<211> LENGTH: 321
<212> TYPE: DNA
<213> ORGANISM: Artificial
<220> FEATURE:
<223> OTHER INFORMATION: nt sequence encoding humanized light chain
      variable domain variant 1

<400> SEQUENCE: 25
aacatcgtga tgacccagtc tccatcctcc ctgtctgcat ctgtaggaga cagagtcacc      60
atcacttgca aggccagtga aaatgtggtg acttatgtat cctggtttca gcagaaacca    120
gggcaggctc ctaagctgct gatctacggt gcatccaatc ggtacactgg ggtcccagac    180
aggttcacag gcagtggatc tgcaacagat ttcactctca ccatcagcag cctgcaggct    240
gaagatgtgg cagattatca ctgtggacag agttacagtt accctctcac tttcggccag    300
gggaccaagc tggagatcaa a                                                321

<210> SEQ ID NO 26
<211> LENGTH: 321
<212> TYPE: DNA
<213> ORGANISM: Artificial
<220> FEATURE:
<223> OTHER INFORMATION: nt sequence encoding humanized light chain
      variable domain variant 2

<400> SEQUENCE: 26
aacatcgtga tgacccagtc tccatcctcc ctgtctgcat ctgtaggaga cagagtcacc      60
```

```
atcacttgca aggccagtga gaatgtggtg acttatgtat cctggtttca gcagaaacca    120
gggcaggctc ctaagctgct gatctacggt gcatccaatc ggtacactgg ggtcccagac    180
aggttcagcg gcagtggatc tgcaacagat ttcactctca ccatcagcag cctgcaggct    240
gaagatgtgg cagattatca ctgtggacag agttacagtt accctctcac tttcggccag    300
gggaccaagc tggagatcaa a                                              321

<210> SEQ ID NO 27
<211> LENGTH: 321
<212> TYPE: DNA
<213> ORGANISM: Artificial
<220> FEATURE:
<223> OTHER INFORMATION: nt sequence encoding humanized light chain
      variable domain variant 3

<400> SEQUENCE: 27
gacatcgtga tgacccagtc tccatcctcc ctgtctgcat ctgtaggaga cagagtcacc     60
atcacttgca aggccagtga gaatgtggtg acttatgtat cctggtttca gcagaaacca    120
gggcaggctc ctaagctgct gatctacggt gcatccaatc ggtacactgg ggtcccagac    180
aggttcagcg gcagtggatc tgggacagat ttcactctca ccatcagcag cctgcaggct    240
gaagatgtgg cagattatca ctgtggacag agttacagtt accctctcac tttcggccag    300
gggaccaagc tggagatcaa a                                              321

<210> SEQ ID NO 28
<211> LENGTH: 321
<212> TYPE: DNA
<213> ORGANISM: Artificial
<220> FEATURE:
<223> OTHER INFORMATION: nt sequence encoding humanized light chain
      variable domain variant 4

<400> SEQUENCE: 28
gacatcgtga tgacccagtc tccatcctcc ctgtctgcat ctgtaggaga cagagtcacc     60
atcacttgca aggccagtga gaatgtggtg acttatgtat cctggtttca gcagaaacca    120
gggcaggctc ctaagctgct gatctacggt gcatccaatc ggtacactgg ggtcccagac    180
aggttcagcg gcagtggatc tgggacagat ttcactctca ccatcagcag cctgcaggct    240
gaagatgtgg caacttatca ctgtggacag agttacagtt accctctcac tttcggccag    300
gggaccaagc tggagatcaa a                                              321
```

MONOCLONAL ANTIBODIES AGAINST THE ACTIVE SITE OF FACTOR XI AND USES THEREOF

FIELD OF THE INVENTION

The present invention relates in general to the fields of medicine and pharmacy, in particular to the field of biopharmaceuticals for use in haematology-coagulation. More specifically, the invention relates to antibodies against the active site of factor XI that inhibit the activation of factor IX by activated factor XI. The antibodies against the active site of factor XI are useful in the prevention and treatment of conditions in which pathological thrombus formation or thrombo-embolism are involved.

BACKGROUND OF THE INVENTION

Coagulation consists of a humoral and a cellular response, and is an essential part of hemostasis, which is the process that stops blood from being lost via a wound or injury. Pathological coagulation or thrombosis refers to clot formation that is not part of a normal hemostatic process and that may result in disease symptoms. Deep venous thrombosis, thrombosis on vascular grafts, thrombosis on an atherosclerotic plaque in a coronary artery, microvascular thrombosis and diffuse intravascular coagulation in sepsis are examples of pathological coagulation. In addition, parts of the pathological thrombus can be released and carried away with the blood flow to plug blood vessels elsewhere in the body such as the lungs or the brains, which process is called embolization. Diseases in which thrombosis with or without embolization play a role, are called thrombo-embolic diseases.

A main treatment of thrombo-embolic diseases consists of the administration of anticoagulant drugs, which drugs inhibit the coagulation system. This system is a set of plasma proteins that circulate as inactive enzymes and cofactors, and that can activate each other in a cascade-like manner. The key enzyme in this cascade is thrombin, which converts soluble fibrinogen into insoluble fibrin, and which activates a number of other coagulation factors including FXI, FVIII and FV, into active species thereby providing amplification of activation (Clotting factors are referred to as FXI, FIX etc.; activated clotting factors as FXIa, FIXa, etc.). Excessive activation of coagulation is prevented by circulating inhibitors such as antithrombin.

A simplified scheme of the coagulation cascade is depicted in FIG. 10. Coagulation occurs via a main or basal pathway and two amplification loops.

Current anticoagulant drugs inhibit the common pathway of coagulation: heparin (via antithrombin) hits thrombin, FXa and FIXa, coumarins inhibit the synthesis of prothrombin, factors VII, IX and X, whereas Low Molecular Weight heparin mainly inhibits FXa. The therapeutic window of these drugs is narrow, and their use may result in severe bleeding adverse events in 1-2% of the patients per year while mild bleeding episodes occur even more frequently. For example, patients treated with anticoagulants because of venous thrombosis have a risk of major bleeding of 7.2 events per 100 person-years and the risk of fatal bleeding is 1.31 per 100 person-years, with a case-fatality rate of 13.4% from major bleeding (Linkins L A, Ann Intern Med 2003; 139:893-900). Therefore, the use of anticoagulants in daily practice has a high risk of bleeding side effects and requires careful monitoring of patients.

Currently, there are no approved anticoagulants that target FXI. This reflects that for long time FXI was considered to play a minor, if any, role in thrombo-embolic processes as the role of FXI in hemostasis was considered to be limited. Indeed, FXI deficiency does not result in a severe bleeding tendency with episodes of spontaneous bleeding in joints and soft tissue, such as hemophilia A and B, but rather is associated with an injury-related bleeding disorder (Duga S, et al., Semin Thromb Hemost 2013; 39:621-31; F Peyvandi et al., Haematologica 2002; 87:512-514). Many FXI deficient persons never experience a severe bleeding episode (Castaman G et al., Haemophilia 2014; 20:106-13). However, several studies have shown that inhibition of the function of FXI in vivo can prevent pathological thrombosis without affecting the bleeding time (Minnema et al., 1998, J Clin Invest. 101:10-14; Gruber and Hanson, 2003, Blood 102:953-955; Tucker et al., 2009, Blood, 113:936-44; Cheng et al., 2010, Blood 116:3981-9; Takahashi et al., 2010, Thromb Res, 125:464-70; van Montfoort et al., 2013, Thromb Haemost 110:1065-73), supporting an important role of FXI in pathologic thrombus formation. Presumably this differential use of FXI in normal hemostasis versus pathologic thrombus formation reflects that normal hemostasis is mainly triggered by high tissue factor (TF) concentrations, and is therefore independent on the FXI amplification loop (see FIG. 10), whereas pathologic thrombus formation starts at low TF concentration. This differential role in normal hemostasis versus thromboembolic processes makes FXI an attractive target for anticoagulation strategies (Lowenberg E C et al., J Thromb Haemost 2010; 8:2349-57). One approach to target FXI is antisense oligonucleotide-based therapy which aims to decrease the synthesis of FXI in the liver. This approach has shown promising results in animal models (Zhang H et al., Blood. 2010; 116:4684-4692; Younis H S et al., Blood 2012; 119:2401-08) as well as in humans (Buller H et al., N Engl J Med 2015; 372: 232-40). However, antisense oligonucleotides to decrease the synthesis of FXI cannot be used in acute thromboembolic conditions, as it takes at least 1-2 weeks to sufficiently lower FXI levels (Younis H S et al., Blood 2012; 119:2401-08). Moreover, long term toxicity is unknown. Hence, there is a need for different approaches to target FXI as anticoagulation strategy. One alternative approach is to apply monoclonal antibodies (mAbs) that block the functional activity of FXI.

The present invention discloses novel anticoagulant drugs that target FXI and have a lower, if any, risk for bleeding. Therefore, clinical use of these novel anticoagulants do not need monitoring of patients. An inhibitor that blocks the active site of FXI/FXIa would be a preferred approach to target FXI. However, FXI is a serine protease and its active site is homologous to that of numerous other serine proteases particularly those of the trypsin family of serine proteases. Other clotting factors, fibrinolytic and complement proteases belong to the same family, and all have a homologous active site. Hence, small molecule inhibitors of FXIa have an inherent risk of toxicity due to cross-reaction with other serine proteases. A mAb that binds to the active site of FXI/FXIa and blocks the conversion of protein and peptide substrates by FXIa, would be a preferred option for therapeutic applications. However, until now such an inhibitory mAb against the active site of FXIa has not been described.

Sinha et al. (J Biol Chem 1985; 260:10714-9) disclose the 5F4 mAb, which appears directed against the light chain of FXIa and which antibody is disclosed to inhibit 100% of FXIa activity. However, Akiyama et al. (J. Clin. Invest.

1986; 78: 1631-1637) have subsequently reported that the 5F4 mAb does not inhibit the chromogenic activity of FXIa and therefore does not bind active site of FXIa. Presumably the 5F4 mAb is directed against an exosite on the light chain of FXIa (Sinha et al., Biochemistry 2007; 46:9830-9).

It is therefore an object of the present invention to provide for antibodies that bind to the serine protease domain of factor XI(a), inhibit the conversion of small chromogenic substrates of factor XIa as well as the conversion of factor IX into factor IXa by factor XIa. The invention further provides for humanized versions of such monoclonal antibodies (mAbs), as well as applications of the antibodies to treat or prevent thrombo-embolic disease.

SUMMARY OF THE INVENTION

In a first aspect the invention relates to an antibody that binds the light chain of factor XI (factor XI). The antibody preferably reduces the chromogenic activity of activated factor XI (factor XIa), whereby preferably the chromogenic substrate is L-pyroglutamyl-L-prolyl-L-arginine-p-nitroaniline. The antibody further preferably cross-competes for the binding to factor XI with an antibody of which the heavy chain variable domain comprises SEQ ID NO: 1 and the light chain variable domain comprises SEQ ID NO: 2.

A preferred antibody according to the invention comprises at least one hypervariable region (HVR) selected from: HVR-H1 comprising the sequence of SEQ ID NO: 3, HVR-H2 comprising the sequence of SEQ ID NO: 4, HVR-H3 comprising the sequence of SEQ ID NO: 5, HVR-L1 comprising the sequence of SEQ ID NO: 6, HVR-L2 comprising the sequence of SEQ ID NO: 7 and HVR-L3 comprising the sequence of SEQ ID NO: 8. More preferably, the antibody comprises 2, 3, 4, 5, or 6 hypervariable regions (HVR) selected from: HVR-H1 comprising the sequence of SEQ ID NO: 3, HVR-H2 comprising the sequence of SEQ ID NO: 4, HVR-H3 comprising the sequence of SEQ ID NO: 5, HVR-L1 comprising the sequence of SEQ ID NO: 6, HVR-L2 comprising the sequence of SEQ ID NO: 7 and HVR-L3 comprising the sequence of SEQ ID NO: 8.

The antibody according to the invention preferably is a mouse, a chimeric or a humanized antibody. Alternatively the antibody can be an antibody fragment is selected from an Fv, a single-chain Fv (scFv), a Fab, a Fab', a (Fab')$_2$ and a nanobody.

A preferred antibody or antibody fragment according to the invention, comprises a heavy chain variable domain comprising an amino acid sequence with at least 95% sequence identity to at least one of SEQ ID NO's: 13-16, and a light chain variable domain of the antibody comprising an amino acid sequence with at least 95% sequence identity to at least one of SEQ ID NO's: 17-20. More preferably, in the antibody or antibody fragment, the heavy chain variable domain of the antibody comprises the amino acid sequence of SEQ ID NO: 16 and the light chain variable domain of the antibody comprises the amino acid sequence of SEQ ID NO: 20.

An antibody according to the invention, preferably comprises a mutation in the hinge region that favors inter-chain disulfide bridging of the heavy chains over intra-chain disulfide bridge formation. More preferably, the mutation is S241P.

In a preferred antibody according to the invention, the antibody comprises a heavy chain constant region that is an IgG4 region, more preferably a human IgG4 region.

It is further preferred that an antibody according to the invention binds the light chain of human FXIa.

In a second aspect, the invention relates to a pharmaceutical composition comprising the antibody or antibody fragment according to the invention, and optionally a pharmaceutically acceptable carrier.

In a third aspect, the invention relates to an antibody, antibody fragment or a pharmaceutical composition according to the invention, for use as a medicament.

In a fourth aspect, the invention relates to an antibody, antibody fragment or a pharmaceutical composition according to the invention for use in preventing or treating at least one of: i) a disease, disorder or condition that is mediated by FXI activation; and ii) a disease, disorder or condition wherein inhibition of FXI has a beneficial effect. Preferably, the disease, disorder or condition is a disease, disorder or condition in which coagulation is involved. More preferably, the disease is a thrombo-embolic disease or an inflammatory disease accompanied by coagulation activation via FXI. Alternatively, the antibody, antibody fragment or a pharmaceutical composition are for a use according to the invention, wherein the use is for preventing or treating a pathological thrombosis or in preventing thrombosis in a subject who is at increased risk of developing thrombosis due to a medical procedure. The use according to the invention can thus be a use for preventing or treating at least one disorder, disease or condition selected from the group consisting of myocardial infarction, ischemic stroke, cardio-embolism due to atrial fibrillation, vascular access thrombosis, deep venous thrombosis, arterial thrombosis, coronary artery thrombosis, atherosclerosis, arthritis, vasculitis, respiratory distress syndrome, ischemic heart disease, ischemic cerebral disease, pulmonary embolism, venous thrombo-embolism resulting from surgery or immobilization, thrombosis and occlusion of synthetic grafts, stents, or AV-fistula, prosthetic heart valves, diffuse intravascular coagulation (DIC), hemodialysis, atrial fibrillation, sepsis, septic shock, organ failure, kidney failure, toxicity induced by the in vivo administration of therapeutic proteins, multiple trauma, ischemia-reperfusion injuries, local undesired fibrin deposition and fibrin deposition in the lung alveoli during adult respiratory distress.

Preferably, the antibody, antibody fragment or pharmaceutical composition are for a use according to the invention, wherein the antibody is administered intravenously intraarterially, intramuscularly or subcutaneously. The intravenous administration preferably is as a bolus infusion or as a continuous infusion over a period of from less than 2 hours to 24 hours.

Preferably, when the antibody, antibody fragment or pharmaceutical composition are for use in preventing, reducing or treating thrombosis (and occlusion) of synthetic grafts, stents, or AV-fistula in a kidney-patient undergoing regular dialysis, wherein the antibody, antibody fragment or composition is administered to the patient in the dialysed body fluid that is returned to the patient.

Alternatively, the antibody, antibody fragment or pharmaceutical composition for a use according to the invention, are for use in preventing or treating thrombosis in a patient with atrial fibrillation, unstable angina pectoris, venous thrombo-embolism, prosthetic heart valves, ischemic heart disease, ischemic cerebral disease, vascular grafts, diffuse intravascular coagulation, sepsis, or a patient undergoing prostate or orthopedic surgery, wherein the binding molecule is administered no more (frequently) than once per 2 weeks.

In a fifth aspect, the invention relates to a nucleic acid molecule comprising a nucleotide sequence encoding an antibody or antibody fragment according to the invention. Preferably, the nucleic acid molecule comprises a nucleotide sequence encoding at least one of the heavy chain variable domain and the light chain variable domain of the antibody. More preferably, in the nucleic acid molecule, the coding nucleotide sequence is operably linked to regulatory sequences for expression of the coding nucleotide sequence in a host cell.

In a sixth aspect, the invention relates to a host cell comprising the nucleic acid molecule according to the fifth aspect.

DESCRIPTION OF THE INVENTION

Definitions

The term "antibody" is used in the broadest sense and specifically covers, e.g. an antibody or fragments thereof, a unibody, a diabody, a triabody, a tetravalent or other multi-valent antibody specifically binding FXI/FXIa and inhibiting the functional activity of FXI/FXIa. The term "antibody" refers to polyclonal antibodies, anti-FXI/FXIa antibody compositions with polyepitopic specificity, monoclonal antibodies (mAbs), including full length or intact monoclonal antibodies which are derived from a phage library, humanized antibodies, human antibodies, synthetic antibodies, chimeric antibodies, single domain antigen binding proteins and fragments of anti-FXI/FXIa antibodies (see below), including Fab, Fab', F(ab')2 and Fv fragments, diabodies, single domain antibodies (sdAbs), single-chain Fv's. Also antibodies made in other animal species such as camelid antibodies or fragments thereof ("Nanobodies") fall within the scope of this application. Furthermore, molecules with antibody-like binding properties such as Designed Repeat Proteins like DARPins (Designed Ankyrin Repeat Proteins) are within the scope of this application. All of these antibody forms are within the scope of the invention as long as they exhibit the desired biological and/or immunological activity. The term "immunoglobulin" (Ig) is used interchangeable with antibody herein. An antibody can be human and/or humanized.

The term "anti-FXI/FXIa antibody" or "an antibody that binds to FXI/FXIa", refers to an antibody that is capable of binding FXI/FXIa with sufficient affinity such that the antibody is useful as a diagnostic and/or therapeutic agent in targeting and inhibiting FXI/FXIa. The binding affinity for native FXI can be similar as that for FXIa, or can be higher for FXIa than native FXI, or higher for FXI as compared to FXIa. In the text the antibody is indicated as anti-FXIa antibody or anti-FXI antibody at other places, but all three types of anti-FXI mAbs are considered to be in the scope of this invention.

Preferably, the extent of binding of an anti-FXI/FXIa antibody to an unrelated, non-FXI protein is less than about 10% of the binding of the antibody to FXI/FXIa as measured, e.g., by a radioimmunoassay (RIA) or ELISA. In certain embodiments, an antibody that binds to FXI/FXIa has a dissociation constant ($K_D$) of ≤1 mM, ≤100 nM, ≤50 nM, ≤10 nM, ≤5 nM, ≤1 nM, or ≤0.1 nM. In certain embodiments, anti-FXIa antibody binds to an epitope of FXIa that is conserved among FXIa from different species.

An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 Daltons. Each L chain is linked to a H chain by one covalent disulfide bond, while the two H chains are linked to each other by one or more disulfide bonds depending on the H chain isotype. IgG4 subclass consists of 2 H chains that can be linked in a non-covalent way. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes.

There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "complementarity determining regions" (CDRs) or "hypervariable regions" (HVRs) that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

A "naked antibody" for the purposes herein is an antibody that is not conjugated to a cytotoxic moiety or radiolabel.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In one embodiment, an antibody fragment comprises an antigen binding site of the intact antibody and thus retains the ability to bind antigen.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments, which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and—binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma and Immunol., 1:105-115 (1998); Harris, Biochem. Soc. Transactions, 23:1035-1038 (1995); Hurle and Gross, Curr. Op. Biotech., 5:428-433 (1994).

The term "hypervariable region", "HVR", when used herein refers to the regions of an antibody variable domain which are hypervariable in sequence and/or form structurally defined loops that are responsible for antigen binding. Generally, antibodies comprise six hypervariable regions; three in the VH (H1, H2, H3), and three in the VL (L1, L2, L3). A number of hypervariable region delineations are in use and are encompassed herein. The hypervariable regions generally comprise amino acid residues from a "complementarity determining region" or "CDR" (e.g., around about residues 24-34 (L), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L), 50-56 (L2) and 89-97 (L3) in the VL, and 26-32 (H1), 52-56 (H2) and 95-101 (H3) in the VH when numbered in accordance with the Chothia numbering system; Chothia and Lesk, J. Mol. Biol. 196:901-917 (1987)); and/or those residues from a "hypervariable loop"/CDR (e.g., residues 27-38 (L), 56-65 (L2) and 105-120 (L3) in the VL, and 27-38 (H1), 56-65 (H2) and 105-120 (H3) in the VH when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L), 63, 74-75 (L2) and 123 (L3) in the VL, and 28, 36 (H1), 63, 74-75 (H2) and 123 (H3) in the VH when numbered in accordance with Honneger, A. and Plunkthun, A. J. (Mol. Biol. 309:657-670 (2001)). The hypervariable regions/CDRs of the antibodies of the invention are preferably defined and numbered in accordance with the Kabat numbering system.

"Framework" or "FR" residues are those variable domain residues other than the hypervariable region residues herein defined.

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity ($K_D$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the affinity constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

A "$K_D$" or "$K_D$ value" can be measured by using surface plasmon resonance assays using a BIAcore™-2000 or a BIAcore™-3000 (BIAcore, Inc., Piscataway, N.J.) at 25° C. with immobilized antigen CM5 chips at ~10-50 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, IM ethanolamine is injected to block unreacted groups. For kinetics measurements, two-fold serial dilutions of the antibody or Fab (0.78 nM to 500 nM) are injected in PBS with 0.05% Tween 20 (PBST) at 25° C. at a flow rate of approximately 25 µl/min. Association rates ($k_{on}$ or $k_a$) and dissociation rates ($k_{off}$ or $k_d$) are calculated using a simple one-to-one Langmuir binding model (BIAcore Evaluation Software version 3.2) by simultaneous fitting the association and dissociation sensorgram. The equilibrium dissociation constant ($K_D$) is calculated as the ratio $k_{off}/k_{on}$. See, e.g., Chen, Y., et al., (1999) J. Mol Biol 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) as described above.

An antibody "which binds" an antigen of interest, i.e. the active center of FXI, is one that binds the antigen with sufficient affinity such that the antibody is useful as a therapeutic agent in inhibiting the functional activity of FXI, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target (which may be determined as described above) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

The term "epitope" is the portion of a molecule that is bound by an antigen binding protein, e.g. an antibody. The term includes any determinant capable of specifically binding to an antigen binding protein, such as an antibody or to a T-cell receptor. An epitope can be contiguous or non-contiguous (e.g., in a polypeptide, amino acid residues that are not contiguous to one another in the polypeptide sequence but that within in context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl, sulfonyl or sulfate groups, and may have specific three dimensional structural characteristics, and/or specific charge characteristics. Generally, antibodies specific for a particular target antigen will preferentially recognize an epitope on the target antigen in a complex mixture of proteins and/or macromolecules.

"Sequence identity" and "sequence similarity" can be determined by alignment of two amino acid sequences or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

Once two amino acid sequences are aligned using any of the above alignment programs, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

DETAILED DESCRIPTION OF THE INVENTION

Anti-FXI Antibodies of the Invention

The present invention relates to means and methods for anti-coagulant therapy targeting FXI. FXI inhibitors have less risk for bleeding side effects as FXI plays a minor role in normal hemostasis. Indeed, FXI deficiency or FXI inhibition in animals has no effect on the bleeding time, in contrast to high dose heparin which markedly prolongs the bleeding time and which is in clinical practice is associated with severe bleeding side effects. Thus, because of its active role in pathologic thrombosis and a minor role, if any, in normal hemostasis, FXI is an attractive target for anti-coagulant therapy. The inventors have developed unique antibodies to inhibit FXI activity in humans.

In a first aspect the present invention relates to a monoclonal antibody (mAb) that specifically binds to the active center of FXI or FXIa and inhibits the functional activity of FXIa. FXI is herein understood as the mammalian plasma coagulation factor XI. Preferably, the antibodies of the invention specifically bind to the serine protease domain of human factor XI and inhibit the conversion of substrates by FXIa.

The antibodies of the present invention inhibit the catalytic center of FXIa, as is identified by their (partial) inhibiting effect on the chromogenic activity of FXIa as determined in a chromogenic assay. Chromogenic substrates consist of small peptides coupled to p-nitroanilide (pNA). Hydrolysis of the substrate releases pNA which can be measured with a spectrophotometer. Specificity of the substrate for certain proteases is dependent on the precise sequence of the peptide linked to pNA. In case of FXIa, the substrate S2366 (L-pyroglutamyl-L-prolyl-L-arginine-p-nitroaniline; Chromogenix, Molndal, Sweden) is appropriate. Measurement of FXIa activity with this substrate can be done using the method described by Minnema M C et al. (Blood 1998; 92:3294-3301).

The antibodies of the invention preferably bind to at least one of FXI and FXIa and inhibit the enzymatic activities of FXIa. These inhibited activities of FXIa preferably include one or more of the conversion of FIX into FIXa, the conversion of FXI into FXIa (during auto-activation of FXI), and that of chromogenic substrates. More preferably, antibodies of the invention inhibit the activity of FXI/FXIa independently of how FXI is activated.

Preferably, the antibody inhibits the activity of FXI/FXIa by binding to or near to the active site located in the serine protease domain of the molecule, more preferably by binding to or near to sites in the serine protease domain that are involved in the interaction with its substrate FIX.

The antibody preferably binds to the native form of FXI as well as to the activated form, FXIa, and inhibits the activity of FXIa by binding to or near to sites that are involved in the interaction with its substrate FIX.

The antibodies of the present invention are thus characterized by their ability to bind to the active site domain of FXI/FXIa, to inhibit the enzymatic activity of FXIa and to inhibit activation of FIX. Said antibodies can be selected by the assessment of their effect in the assays as described in the Examples herein. In particular anti-FXI antibodies can be selected by the assessment of their effect on the clotting activity of the coagulation system as determined with an activated partial thromboplastin time (APTT) in human plasma. The functional properties of FXI-antibodies of the invention may be tested by adding these to fresh human plasma, followed by measurement of the APTT in a regular clotting assay. In case of an antibody that inhibits the activity of FXI/FXIa, a prolongation of the APTT is observed. As controls normal plasma (normal APTT) and FXI-deficient plasma (prolonged APTT) are tested. These clotting assays are well known in the art (see also Examples herein).

A preferred antibody of the invention is an antibody that: a) binds the light chain of activated factor XI, b) reduces the chromogenic activity of factor XIa on L-pyroglutamyl-L-prolyl-L-arginine-p-nitroaniline, and c) cross-competes for the binding to factor XI with an antibody of which the heavy chain variable domain comprises SEQ ID NO: 1 and the light chain variable domain comprises SEQ ID NO: 2.

The antibody of the invention preferably specifically binds the light chain of activated factor XI as herein defined above. Preferably the antibody thus binds the active center of FXI with sufficient affinity such that the antibody is useful as a therapeutic agent in inhibiting the functional activity of FXI in a chromogenic assay as described above. Preferably the antibody does not significantly cross-react with other proteins. Preferably, an antibody of the invention will bind to FXI with an affinity less than 100, 50, 10 or 5 nM, more preferably less than 1 nM. Specificity of an antibody to FXI can be determined in any suitable manner known per se in the art, including plasmon surface resonance and/or binding assays such as enzyme immunoassays.

The antibody of the invention preferably reduces the chromogenic activity of factor XIa on L-pyroglutamyl-L-prolyl-L-arginine-p-nitroaniline (S2366) as chromogenic substrate. Preferably the antibody reduces the chromogenic activity of factor XIa on the S2366 substrate by at least 2, 5, 10, 20 or 50%.

The antibody of the invention preferably cross-competes for the binding to factor XIa with an antibody of which the heavy chain variable domain comprises SEQ ID NO: 1 and the light chain variable domain comprises SEQ ID NO: 2. When used herein in the context of two or more antibodies, the term "competes with" or "cross-competes with" indicates that the two or more antibodies compete for binding to FXI, e.g. compete for FXI binding in the ELISA described in Example 1.4 herein. For some pairs of antibodies, competition in the assay of Example 1.4 is only observed when one antibody is coated on the plate and the other is used to compete, and not vice versa. The term "competes with" when used herein is also intended to cover such combinations antibodies. An antibody of the invention that cross-competes for the binding to factor XIa with an antibody defined by the variable domains of SEQ ID NO.'s: 1 and 2, preferably reduces the binding of a thus defined antibody to FXIa in an ELISA by at least 2, 5, 10, 20 or 50%.

In one embodiment, the antibody of the invention inhibits the functional activity of FXI/FXIa preferably is a molecule that produces at least 10, 20, 50 or 90% inhibition of FXI activity at a concentration of about 25-100 nM in an APTT assay. More preferably, the molecule produces at least 95% inhibition of FXI activity at a concentration of about 25-100 nM in an APTT assay.

Preferably, the antibody of the invention comprises at least one hypervariable region (HVR) selected from: HVR-H1 comprising the sequence of SEQ ID NO: 3, HVR-H2 comprising the sequence of SEQ ID NO: 4, HVR-H3 comprising the sequence of SEQ ID NO: 5, HVR-L1 comprising the sequence of SEQ ID NO: 6, HVR-L2 comprising the sequence of SEQ ID NO: 7 and HVR-L3 comprising the sequence of SEQ ID NO: 8. More preferably, the antibody comprises 2, 3, 4, 5, or 6 hypervariable regions (HVR) selected from: HVR-H1 comprising the sequence of SEQ ID NO: 3, HVR-H2 comprising the sequence of SEQ ID NO: 4, HVR-H3 comprising the sequence of SEQ ID NO: 5, HVR-L1 comprising the sequence of SEQ ID NO: 6, HVR-L2 comprising the sequence of SEQ ID NO: 7 and HVR-L3 comprising the sequence of SEQ ID NO: 8.

Preferably, the antibody of the invention is a mouse, a chimeric or a humanized antibody, or the antibody is an antibody fragment is selected from an Fv, a single-chain Fv (scFv), a Fab, a Fab', a (Fab')$_2$ and a nanobody.

A preferred antibody or antibody fragment according to the invention comprises an amino acid sequence with at least 80, 85, 90, 95, 96, 97, 98, 99 or 100% sequence identity to at least one of SEQ ID NO's: 13-16, and wherein the light chain variable domain of the antibody comprises an amino acid sequence with at least 80, 85, 90, 95, 96, 97, 98, 99 or 100% sequence identity to at least one of SEQ ID NO's: 17-20. More preferably, the heavy chain variable domain of the antibody comprises the amino acid sequence of SEQ ID NO: 16 and the light chain variable domain of the antibody comprises the amino acid sequence of SEQ ID NO: 20.

The present invention also provides antibodies comprising functional variants of the heavy chain variable domain, the light chain variable domain, or one or more HVRs of the antibodies of the examples. A functional variant of a heavy chain variable domain, light chain variable domain, or one or more HVRs used in the context of an anti-FXI antibody still allows the antibody to retain at least a substantial proportion (at least about 50%, 60%, 70%, 80%, 90%, 95% or more) of the affinity/avidity and/or the specificity/selectivity of the parent antibody and in some cases such an anti-FXI antibody may be associated with greater affinity, selectivity and/or specificity than the parent antibody. Such functional variants typically retain significant amino acid sequence identity to the parent antibody as may be determined as described herein above.

The sequence of HVR variants may differ from the sequence of the HVR of the parent antibody sequences through mostly conservative substitutions; e.g. at least about 35, 50, 60, 70, 75, 80, 85, 90, 95, 96, 97, 98 or 99% of the substitutions in the variant are conservative amino acid residue replacements. The sequence of HVR variants may differ from the sequence of the HVR of the parent antibody sequences through mostly conservative substitutions; e.g. at least 10, 9, 8, 7, 6, 5, 4, 3, 2 or 1 of the substitutions in the variant are conservative amino acid residue replacements. In the context of the present invention, conservative substitutions may be defined by substitutions within the classes of amino acids reflected in one or more of the following three tables:

Amino Acid Residue Classes for Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine. Additional groups of amino acids may also be formulated using the principles described in, e.g., Creighton (1984) Proteins: Structure and Molecular Properties (2d Ed. 1993), W.H. Freeman and Company.

In one embodiment of the present invention, conservation in terms of hydropathic/hydrophilic properties and residue weight/size also is substantially retained in a variant HVR as compared to a HVR of an antibody of the examples (e.g., the weight class, hydropathic score, or both of the sequences are at least 50, 60, 70, 75, 80, 85, 90, 95, 96, 97, 98 or 99% retained). For example, conservative residue substitutions may also or alternatively be based on the replacement of strong or weak based weight based conservation groups, which are known in the art.

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45, 55, 65, 75, 85, 90, 95 or 99% similarity to the parent peptide.

In a one embodiment of the invention, the antibody comprises a mutation in the hinge region that favors interchain disulfide bridging of the heavy chains over intra-chain disulfide bridge formation. Preferably, the mutation is S241P as described by Angel et al. (1993, Mol Immunol 30:105-8).

In another embodiment of the invention, the antibody comprises a heavy chain constant region that is an IgG4 region, preferably a human or humanized IgG4 region, an murine IgG1 region, an IgG1 region, preferably a human or humanized IgG1 region, more preferably an IgG1 region mutated in the constant region to reduce or prevent complement activation or Fc receptor interactions. Alternatively, the antibody the antibody is a monomeric IgM antibody subunit or a monomeric IgA antibody subunit, preferably a monomeric human(ized) IgM antibody subunit or a monomeric human(ized) IgA antibody subunit.

Generating Antibodies of the Invention

MAbs of the present invention can be obtained by isolating immune cells from an animal immunized with human FXI/FXIa, or parts of these molecules, and immortalization of these cells to yield antibody secreting cell lines such as hybridomas. Human FXI, FXIa, fragments thereof such as of the isolated serine-protease domain of FXI, and/or synthetic peptides comprising FXI amino acid sequences, isolated according to a variety of purification methods may be used to immunize an appropriate host animal. Cell lines that produce the desired antibodies can be identified by screening culture supernatants for the presence of antibody activity, and by establishment of the effect of the selected antibody on the functional activity of FXI.

MAbs can be produced with various techniques well understood by those having ordinary skill in the art. Intended to fall in the scope of this application is any antibody or fragment thereof, independently of how it is made or manufactured, that blocks the activity of human FXI/FXIa by binding to the active site in the serine protease domain of FXI/FXIa and blocking the conversion of the substrates by FXIa. Localization of the epitope for the mAb in the active site is confirmed by demonstrating that the mAb (partially) inhibits the chromogenic activity of FXIa.

A variety of immunization protocols both in vivo in various animals as well as in vitro with lymphocytes, human or murine or other, may be employed, and are well known to those skilled in the art. Human lymphocytes from patients with antibodies against human FXI also can be used to generate mAbs, for example from persons deficient for FXI who have developed antibody responses against administered exogenous FXI (Salomon O et al., Blood 2003; 101: 4783-8) or have acquired FXI deficiency for other reasons.

The initial screening step of culture supernatants of hybridomas obtained by fusion of lymphocytes of mice immunized with FXI, FXIa, parts thereof, or with FXI peptides, with an appropriate fusion partner, is preferably done by an enzyme-linked immunosorbent assay (ELISA). This assay is known to those skilled in the art. Subsequently, the effect of the antibody on the activity of FXI(a) is tested. A convenient assay is to test their effect on the activated partial thromboplastin time (APTT). Antibodies that block the activity of FXI/FXIa will prolong the APTT when added to human plasma. Localization of the epitope for the mAb or fragments thereof can be detected by assessing the effect of the mAbs on the chromogenic activity of FXIa.

Compositions Comprising the Antibodies of the Invention

In a second aspect, the invention pertains to a pharmaceutical composition comprising an antibody or antibody fragment as herein defined above. The pharmaceutical composition further preferably comprises at least one pharmaceutically acceptable carrier. The pharmaceutically acceptable carrier such as an adjuvant, or vehicle, is for administration of the antibody or antibody fragment to a subject. Said pharmaceutical composition can be used in the methods of treatment described herein below by administration of an effective amount of the composition to a subject in need thereof. The term "subject", as used herein, refers to all animals classified as mammals and includes, but is not restricted to, primates and humans. The subject is preferably a male or female human of any age or race.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration (see e.g. "Handbook of Pharmaceutical Excipients", Rowe et al eds. 7$^{th}$ edition, 2012, www.pharmpress.com). The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter ions such as sodium; metal complexes (e.g. Zn-protein complexes); and/or non-ionic surfactants such as TWEEN™, PLURONICS™ or polyethylene glycol (PEG).

The antibodies of the invention may be in the same formulation or may be administered in different formulations. Administration can be concurrent or sequential, and may be effective in either order.

In a further embodiment an antibody of the invention is modified to achieve a desired in vivo serum half-life. For this purpose a polyalkyleneglycol group (e.g. polyethyleneglycol (PEG) group, polypropylene glycol, polybutylene glycol) or a serum protein such as e.g. serum albumin or transferrin can be linked or conjugated to the antibody and/or the amino acid sequence of the antibody can be modified. In particular the amino acid sequence of the constant domains of an antibody that is an antibody can be modified (e.g. introducing amino acid substitutions, deletions and/or insertions). Any of these modifications can thus be used to increase the in vivo serum half-life of the antibody to more than 1, 2, 5, 10 or 20 days. As will be understood by the skilled person, a modification of the antibody of the invention that to increases its half-life will allow the antibody to be administered at a lower dose and/or at a reduced frequency in case of repeated administrations.

The pharmaceutical composition may be administered by any suitable route and mode, including intravenous or subcutaneous injection or infusion. As will be appreciated by the skilled artisan, the route and/or mode of administration will vary depending upon the desired results. For parenteral administration, the mAb will be formulated in an injectable form combined with a pharmaceutically acceptable parenteral vehicle. Such vehicles are well-known in the art and examples include saline, dextrose solution, Ringer's solution and solutions containing small amounts of human serum albumin. Typically, the mAb or fragments thereof will be formulated in such vehicles at a concentration of from about 20 mg to about 100 mg per ml. In one embodiment of this invention the antibody is administered by intravenous injection.

Use of the Antibodies of the Invention

In a third aspect, the invention relates to an antibody or antibody fragment as herein defined above, or a pharmaceutical composition comprising said antibody or antibody fragment, for use as a medicament.

In a fourth aspect, the invention pertains to methods of preventing or treating a disease, disorder and/or condition that is mediated by FXI activation and/or wherein inhibition of FXI has a beneficial effect. The methods preferably comprise the step of administering to a subject an antibody or antibody fragment as disclosed herein above, in an amount effective to treat or prevent the disease, disorder and/or condition. Thus in this aspect the invention relates to an antibody or antibody fragment as herein defined above, or a pharmaceutical composition comprising said antibody or antibody fragment, for use in preventing or treating at least one of: i) a disease, disorder or condition that is mediated by FXI activation; and ii) a disease, disorder or condition wherein inhibition of FXI has a beneficial effect. It is understood herein that preventing or treating a disease, disorder and/or condition means reducing the risk that disease, disorder and/or condition or symptoms associated with the disease, disorder and/or condition occur. Preferably in this aspect, the disease, disorder or condition is a disease, disorder or condition in which coagulation is involved. More preferably, the disease is a thrombo-embolic disease or an inflammatory disease mediated by coagulation activation via FXI. Thus in these embodiments, the antibody of the invention is used for preventing or treating a pathological thrombosis or in preventing thrombosis in a subject who is at increased risk of developing thrombosis due to a medical procedure. Preferably, in these embodiments, the use is for preventing or treating at least one disorder, disease or condition selected from the group consisting of myocardial infarction, ischemic stroke, cardio-embolism due to atrial fibrillation, vascular access thrombosis, deep venous thrombosis, arterial thrombosis, coronary artery thrombosis, atherosclerosis, arthritis, vasculitis, respiratory distress syndrome, ischemic heart disease, ischemic cerebral disease, pulmonary embolism, venous thrombo-embolism resulting from surgery or immobilization, thrombosis and occlusion of synthetic grafts, stents, or AV-fistula, prosthetic heart valves, diffuse intravascular coagulation (DIC), hemodialysis, atrial fibrillation, sepsis, septic shock, organ failure, kidney failure, toxicity induced by the in vivo administration of therapeutic proteins, multiple trauma, ischemia-reperfusion injuries, local undesired fibrin deposition and fibrin deposition in the lung alveoli during adult respiratory distress.

According to another embodiment the antibodies of the invention can be used for inhibiting coagulation in various human diseases. As a result the inhibitors of the present invention can be used for the preparation of a medicament for attenuating thrombo-embolic disorders by inhibiting coagulation in vivo. The antibodies can be used alone or in combination with other drugs.

In a further embodiment the antibodies of the invention can be used alone or in combination with other drugs in any suitable ratios, for the preparation of a medicament to treat a subject suffering of a disease or disease symptoms resulting from pathologic thrombosis and or embolism, or at risk with respect to such a disease.

Thus, in the present invention, patients suffering from a disease involving coagulation-mediated damage can be administered an effective amount of the anti-FXI antibody of the invention so that activation of FXI is inhibited. By "effective amount" is meant a concentration of the antibody, which is capable of inhibiting thrombin generation and the formation of fibrin.

Treatment (prophylactic or therapeutic) will generally consist of administering an antibody of the invention, e.g. a composition comprising the antibody of a fragment thereof, parenterally, preferably intravenously, intra-arterially, intramuscularly or subcutaneously. Gruber and Hanson (Gruber and Hanson, 2003, Blood 102:953-955) administered goat anti-FXI antibodies at a dose of 16-50 mg per kg to achieve sufficient inhibition of FXI in baboons. In contrast, the dose and administration regimen of an antibody of the invention preferably is in the range of a dosage that is equivalent to a dosage of 0.5-10 mg of IgG per kg body weight per week. More preferably, an antibody of the invention is administered at a dosage that is equivalent to a dosage of less than 18, 16, 14, 12, 10 8, 6 or 4 mg of IgG per kg body weight per week and/or at a dosage that is equivalent to a dosage of at least 0.6, 0.8, 1.0, 1.2, 1.5, 2, or 4 mg of IgG per kg body weight per week. It is understood that in case of e.g. antibody fragments the dosage to be used will be the molar equivalent of the corresponding amount of mg of an IgG molecule per kg body weight as indicated.

It is further understood that the dosage regimes for the antibodies of the invention are based on the average serum half-life of a human antibody of about 7 days. The skilled person will know how to adjust the dosage regime of antibodies with a half-life that is shorter or longer than 7 days.

In a further embodiment, an antibody of the invention, when administered to a human patient via intravenous infusion, provides at least 50, 60, 70, 80 or 90% inhibition of FXI, preferably at dosages below 10 or 5 mg/kg of body weight. Alternatively, an antibody of the invention, when administered to a human patient via intravenous infusion, provides a prolongation of aPTT by at least a factor 1.1, 1.2, 1.25, 1.3, 1.4, 1.5, 1.6, 1.7, 1.8, 2.0, 2.2, 2.5, 3 or 4, preferably at dosages below 10 or 5 mg/kg of body weight.

In a further embodiment, an antibody of the invention, when administered to a human patient via intravenous infusion, provides therapeutic benefits at dosages below 10 or 5 mg/kg of body weight.

In one embodiment, the equivalent of the above-indicated weekly dosages of the antibodies according to the invention can be administered by infusion. Such administration can be repeated as many times as desired. The administration may be performed by bolus injection or infusion or continuous infusion over a period of from less than 2 hours to 24 hours, such as from 2 to 12 hours. In another embodiment, the antibodies of the invention can be administered by slow continuous infusion over a long period, such as more than 24 hours. Such regimen may be continued or repeated one or more times as necessary, for example, after 6 months or 12 months. The dosage can be determined or adjusted by measuring the amount of circulating anti-FXI antibodies upon administration in a biological sample by using anti-idiotypic antibodies which target the mAbs of the invention. In yet another embodiment, the antibodies can be administered by maintenance therapy, such as, e.g., once per 1, 2, 3, 4 or 6 weeks for a period of 6 months or more.

In one embodiment, the antibody of the invention is used in the prevention or reduction of thrombosis (and occlusion) of synthetic grafts, stents, or AV-fistula in e.g. patients undergoing regular dialysis. In these patients the antibody may be administered at least weekly or several times (e.g. 2, 3 or 4) per week, preferably when the patients are undergoing dialysis. In a preferred embodiment, the antibody is administered to the patient through the dialysis apparatus, e.g. in the dialysed body fluid that is returned to the patient.

In another embodiment, the antibody of the invention is administered to a patient with no regular parenteral access that require nonetheless continuous anticoagulant therapy, such as e.g. in patients with atrial fibrillation, unstable angina pectoris, deep venous thrombosis, diffuse intravascular coagulation, prostate surgery, orthopedic surgery, particularly of the hip or knee, and other thrombo-embolic disorders. In these patients preferably a certain number of administrations of the antibody per time period is applied, e.g. once per 2, 3, 4 or 6 weeks.

Based on the common general knowledge, a person skilled in the art will be able to select a suitable method for administering the antibodies of the invention to yield sufficiently high levels of the antibodies either in the circulation or locally to achieve at least one of as at least one of (a) substantial blockade of FXI activity, and (b) a substantial blockade of thrombin generation for the desired prophylactic or therapeutic effect as required in any given disease, disorder and/or condition that is mediated by FXI activation and/or wherein inhibition of FXI has a beneficial effect.

Production and Purification of the Antibodies of the Invention

Anti-FXI antibodies of the invention can be prepared by any of a number of conventional techniques. They will usually be produced in recombinant expression systems, using any technique known in the art. See e.g. Shukla and Thömmes (2010, "Recent advances in large-scale production of monoclonal antibodies and related proteins", Trends in Biotechnol. 28(5):253-261), Harlow and Lane (1988) "Antibodies: A Laboratory Manual", Cold Spring Harbor Laboratory Press, Cold Spring Harbor, N.Y., and Sambrook and Russell (2001) "Molecular Cloning: A Laboratory Manual ($3^{rd}$ edition), Cold Spring Harbor Laboratory, Cold Spring Harbor Laboratory Press, NY. Any expression system known in the art can be used to make the recombinant polypeptides of the invention. In general, host cells are transformed with a recombinant expression vector that comprises DNA encoding a desired polypeptide.

In one aspect the invention therefore relates to nucleic acid molecules comprising nucleotide sequences encoding an anti-FXI antibody of the invention. One nucleotide sequence encodes a polypeptide comprising at least the variable domain of the light chain of an anti-FXI antibody of the invention, another nucleotide sequence encodes a polypeptide comprising at least the variable domain of the heavy chain of an anti-FXI antibody of the invention. A preferred nucleic acid molecule is an expression vector wherein the nucleotide sequences encoding the antibody polypeptides of the invention are operably linked to expression regulatory sequences, such as e.g. a promoter and a signal sequence.

In another aspect, the invention pertains to a cell comprising a nucleic acid molecule as defined above in this section. The cell preferably is an isolated cell or a cultured cell. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (Gluzman et al., 1981, Cell 23:175), L cells, 293 cells, C127 cells, 3T3 cells, Chinese hamster ovary (CHO) cells, HeLa cells, BHK cell lines, and the CVI/EBNA cell line derived from the African green monkey kidney cell line CVI as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, New York, 1985).

The transformed cells can be cultured under conditions that promote expression of the polypeptide. Thus in one aspect the invention relates to a method for producing an anti-FXI antibody of the invention, the method comprising the step of cultivating a cell comprising at least one expression vector as defined herein, under conditions conducive to expression of the polypeptide and, optionally, recovering the polypeptide.

An anti-FXI antibody of the invention can be recovered by conventional protein purification procedures, including e.g. protein A-Sepharose, hydroxylapatite chromatography, gel electrophoresis, dialysis, or affinity chromatography (see e.g. Low et al., 2007, J. Chromatography B, 848:48-63; Shukla et al., 2007, J. Chromatography B, 848:28-39) including e.g. affinity chromatography using CaptureSelect™ ligands offer a unique affinity purification solution based on Camelid-derived single domain (VHH) antibody fragments (see e.g. Eifler et al., 2014. Biotechnology Progress DOI: 10.1002/btpr. 1958). Polypeptides contemplated for use herein include substantially homogeneous recombinant anti-FXI antibody polypeptides substantially free of contaminating endogenous materials.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

Effects of the anti-FXI mAb 34.2 on A) the chromogenic activity of FXIa and B) the conversion of FIX by FXIa. A) MAb anti-FXI 34.2 inhibits the chromogenic activity of FXIa. Purified FXIa (~3 nM) was incubated with purified anti-FXI mAb 34.2 at 25 and 50 nM, as well as with control mAbs. The activity of FXIa was then assessed with the chromogenic substrate S2366. B) MAb anti-FXI 34.2 inhibits the conversion of FIX by FXIa. Purified FXIa was incubated with purified anti-FXI mAb. The activity was then assessed by incubation with purified FIX. Generation of FIXa was then monitored by incubation with FX. Subsequently FXa levels in the mixtures were measured with the chromogenic substrate S2222. FXIa not incubated with mAb was set at 100%.

FIG. 5. Effect of mAb anti-FXI 34.2 in vivo. A) Effect of mAb anti-FXI 34.2 on IVC thrombosis in mice. FXI-/- mice were given human FXI followed by injection of saline or mAb anti-FXI 34.2 (8 mg/kg). Thrombosis was then induced by 3 minutes application of a filter paper soaked in 10% FeCl3 to the IVC. Venous blood flow was measured for 30 minutes. Data represent the mean and SD of 5 animals. B) MAb anti-FXI 34.2 does not affect tail bleeding time in mice, in contrast to enoxaparin which prolongs tail bleeding time. FXI-/- mice were given human FXI followed by a single dose of either saline (control), enoxaparin (1 mg/kg) or mAb anti-FXI 34.2 (8 mg/kg). Subsequently, tail bleeding was induced and the time until bleeding stopped was recorded in seconds. Each symbol represents one animal, the horizontal line indicates the median.

FIG. 6. A) Effect of the A) chimeric mouse-human anti-FXI 34.2 or B) purified composite human anti-human FXI mAbs on the aPTT of human plasma.

A) Chimeric mAb was added to human plasma at the indicated concentrations. Subsequently, the aPTT of the mixtures was determined. B) The effects of original mouse mAb anti-FXI 34.2 and the mouse-human chimeric antibody are shown for comparison. NPP=normal pooled plasma (without mAb). MAbs anti-C2-60 is a control mAb, mAbs anti-FXI-20D4 and anti-FXI-100 are non-inhibitory anti-FXI mAbs that were included as controls.

FIG. 7. A) Proliferation indexes on days 5 to 8 observed upon incubation of PBMC from 20 donors with A) mAb VH4Vκ4 or B) mouse-human chimeric mAb anti-FXI 34.2. A stimulation index ≥2 is considered to be positive. Borderline proliferation is indicated with an asterix.

FIG. 8. Effect of mAb VH4Vκ4 on thrombin generation in plasma induced by A) aPTT reagent, B) 5 pM TF, C) 1 pM TF, or D) 0.25 pM TF. MAb VH4Vκ4 was added to pooled normal human plasma to a final concentration as indicated. aPTT reagent (A) or a final conc. of 5 pM TF (B), 1 pM TF(C) or 0.25 pM TF (D) was added and the generation of thrombin was measured in real time. X-axis represent time (minutes), Y-axis is thrombin concentration in plasma at the indicated time (nM).

Figure 9:
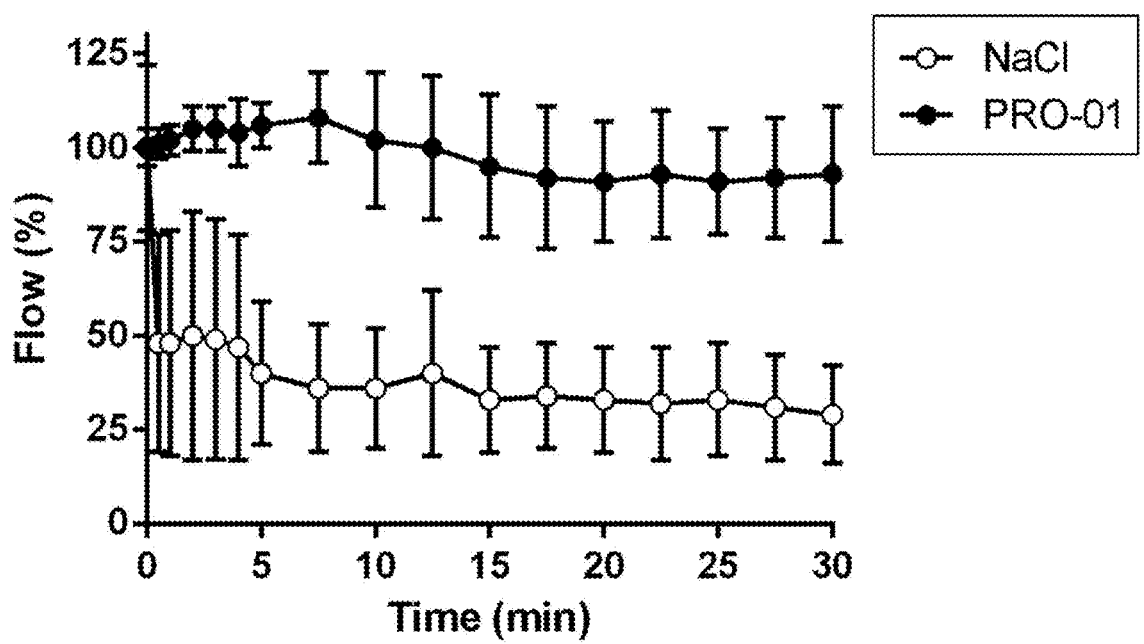

FIG. 9. Effect of the mAb VH4Vκ4 on experimental IVC thrombosis in mice. FXI-/- mice were given human FXI followed by a single dose of saline or mAb VH4Vκ4 (8 mg/kg). Thrombosis was then induced by 3 minutes application of a filter paper soaked in 10% FeCl3 to the inferior vena cava (IVC). Venous blood flow was measured for 30 minutes. Data represent the mean and SEM of 6 animals. The saline control is the same as in FIG. 5A.

Figure 10:
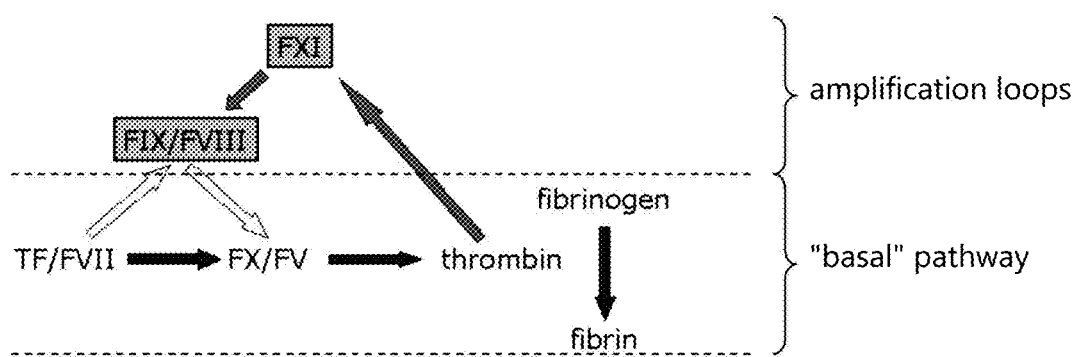

FIG. 10. Simplified scheme of coagulation. For clarity, important components such as phospholipid membranes, regulatory proteins such as antithrombin and TFPI, and the protein C system are not depicted.

EXAMPLES

1. Materials and Methods
1.1 Materials

Human coagulation factors FXI, FX and FIX were purchased from Haematologic Technologies, Inc. (Essex Junction, Vt., USA). Plasma FXI was also obtained from LFB (Hemoleven; LFB, Les Ulis, France). In addition, FXI from other sources (FXI purified from plasma or recombinant human FXI obtained from Prof J C Meijers, Amsterdam) was used as the source of FXI is irrelevant for the outcome of the experiments disclosed below. Prekallikrein (PK) was obtained from Merck Millipore, Darmstadt, Germany. Patromtin SL or Kaolin STA (Stago) (an aPTT reagent), recombinant Innovin and FXI-deficient plasma were obtained from Siemens Healthcare Diagnostics (Marburg, Germany). Thrombin Calibrator and FluCa kit were obtained from Thrombinoscope BV, Maastricht, The Netherlands. Fluorogenic substrate Z-Gly-Gly-Arg-AMC was purchased from Bachem, Bubendorf, Switzerland. Phospholipids (PC/PS/PE, 40/40/20) were obtained from Avanti Polar Lipids, Alabaster, Ala. The chromogenic substrates S2366 and S2222 were obtained from Chromogenix (Milano, Italy). Recombinant fusion proteins of tPA and individual apple domains of FXI were prepared as described (van Montfoort M L et al., Thromb Haemost 2013; 110: 1065-73). Enoxaparin (Clexane) was obtained from Sanofi-Aventis (Paris, France).

1.2 Generation of Mouse mAbs Against Human FXI

MAbs against FXI were generated by conventional methods after injection of mice with purified human plasma human FXI. Briefly, BALB/c mice (females, 6-8 weeks of age; Charles River Laboratories) were subcutaneously injected with purified FXI in complete Freund's adjuvant (each mouse with 25 µg of FXI in 250 µL phosphate buffered saline, pH 7.4 (PBS), mixed with 250 µL complete Freund's adjuvant (Sigma)) on Day 0. Antibody responses in mice were then boosted by subcutaneous injections of purified FXI in incomplete Freund's adjuvant (each mouse with 25 µg FXI in 250 µL PBS mixed with 250 µL incomplete Freund's adjuvant (Sigma)) on Day 21 and Day 42, and by intraperitoneal injections with FXI without adjuvant (each mouse with 25 µg FXI in 250 µL PBS) on Day 63 and on Day 64.

On day 67, splenocytes from immunized mice were fused with SP2/0-Ag14 myeloma cells using standard hybridoma technology originally described by Kohler and Milstein (1975, Nature; 256:495-7). Briefly, immunized mice were sacrificed. Splenocytes were teased from spleens, and washed in serum-free opti-MEM® I medium with GlutaMax (Invitrogen/Life Technologies Corp). Logarithmically growing SP2/0-Ag14 myeloma cells were washed in serum-free medium and added to the splenocytes at a 5:1 ratio of splenocytes-to-myeloma cells. The cells were then pelleted, and the supernatant was removed. One ml of a 37% (w/v) solution of polyethylene glycol 4000 (Merck) was then added dropwise over a 60 sec period, after which the cells were incubated for another 60 sec at 37° C. Eight ml serum free medium, followed by 5 ml opti-MEM I medium with GlutaMax/10% (v/v) fetal calf serum (FCS; Bodinco), was then slowly added with gentle agitation. After 30 minutes at room temperature (RT), the cells were pelleted, washed in opti-MEM I with GlutaMax/10% FCS to remove residual polyethylene glycol, and finally plated at a concentration of 105 cells/200 µl per well in aminopterin selection medium, i.e., opti-MEM I medium with GlutaMax/10% FCS supplemented with 50× Hybri-Max™ aminopterin (a de novo DNA synthesis inhibitor; Sigma). From Day 7 of the fusion experiment, aminopterin selection medium was replenished every 2-3 days, and on Day 13, aminopterin selection medium was replaced by opti-MEM I with GlutaMax/10% FCS.

From Day 13 after fusion, supernatants from hybridomas were screened for anti-FXI antibody production using an ELISA with purified plasma FXI coated on 96-wells plates. The screening ELISA was performed as follows. Human FXI was used for coating (1 µg/ml in PBS; 100 µl/well). After extensive washing with PBS/0.05%, w/v, Tween 20, plates were blocked with PBS/0.05% Tween 20/1%, w/v, bovine serum albumin (BSA; Roche) for 1 hour at RT. Subsequently, plates were incubated with 100 µl undiluted hybridoma supernatant/well for 1 hour at RT. After extensive washing in PBS/0.05% Tween 20, binding of antibodies was determined with 1:5000 diluted horseradish peroxidase-conjugated goat anti-mouse Fcγ-specific antibodies (Jackson ImmunoResearch) for 1 hour at RT, followed by a ready-to-use solution of TMB substrate (Invitrogen) for colorimetric detection. After adding 1 M $H_2SO_4$, optical densities were measured at a wavelength of 450 nm (reference wavelength of 655 nm) using a microplate reader (BioRad). Hybridomas positive in this ELISA were expanded and cryopreserved.

Hybridomas that produced a mAb that prolonged the aPTT were further cultured. The mouse IgG was purified from this supernatant by protein G chromatography using prepacked columns (Pharmacia Healthcare) according to manufacturer's instructions.

Cross-reactivity of anti-FXI mAbs with prekallikrein (PK) was tested in an ELISA which was comparable to the ELISA described above except that purified PK at 100 ng per well was used for coating instead of FXI, the blocking step with BSA was omitted and that goat anti-mouse Fcγ-specific antibodies (Santa Cruz) at a 1/1000 dilution were used to detect bound mAb. Wells coated with BSA were included as control.

1.3 Surface Plasmon Resonance

Surface plasmon resonance was on a Biacore 2000 (GE Healthcare) equipped with a research-grade cm5 sensor chip to assess the affinity constants of the mAbs for FXI. Factor XI was immobilized using amine-coupling chemistry. the surface was activated for 7 min with a 1:1 mixture of 0.1 M N-hydroxysuccinimide and 0.1 M 3-(N,N-dimethylamino) propyl-N-ethylcarbodiimide at a flow rate of 10 l per min. The ligand at a concentration of 10 µg/ml in 10 mM sodium acetate, pH 5.5, was immobilized at a density of 1000 ru. An untreated flow cell served as a reference surface. All the surfaces were blocked with a 7 min injection of 1 M ethanolamine, pH 8.0. The following protocol was used to assess kinetic binding of the mAbs to FXI. The analyte was injected over the two flow cells at concentrations ranging between 6.25-100 nM in 10 mM HEPES, 150 mM NaCl, 0.01% Tween 20, pH 7.4, at a flow rate of 60 µl/min and at a temperature of 20° C. The complex was allowed to associate and dissociate for 360 and 600 seconds, respectively. The surfaces were regenerated with a 10 seconds injection of 50 mM NaOH. Triplicate injections (in random order) of each sample and a buffer blank were flowed over the two surfaces. Data were collected at a rate of 1 Hz. The data were fit to a simple 1:1 interaction model using the global data analysis option available within BiaEvaluation 4.1 software.

1.4 Localisation of the Epitopes for the Inhibitory mAbs on FXI Domains

The individual apple domains of FXI were expressed as fusion proteins with tPA as described (Meijers J C et al., Biochemistry 1992; 31:4680-4). Binding of the mAbs to these fusion proteins was assessed using an ELISA in which the four fusion proteins as well as purified plasma FXI were coated on ELISA plates at 1 µg/ml and subsequently incubated with the different mAbs (van Montfoort et al., Thromb Haemost 2013; 110:1065-73). Binding of mAbs to the fusion proteins was then measured with peroxidase-conjugated anti-mouse IgG, and antibodies bound to the plates were detected by incubation with ortho-phenylenediamine-dihydrochloride (OPD). Results were expressed as OD at 490 nm.

1.5 Coagulation Assays

Prothrombin time (PT) and activated partial thromboplastin time (aPTT) were measured on an automated coagulation analyzer (Behring Coagulation System) with reagents and protocols from the manufacturer (Siemens Healthcare Diagnostics).

To test the effects of the mAbs, hybridoma supernatant was mixed with an equal volume of fresh human plasma. The effect of hybridoma supernatants on the activity of FXI was quantified by comparison with FXI-deficient plasma mixed 1:1 with dilutions of purified FXI (25 nM and lower). The results were expressed as % inhibition of FXI, with FXI-deficient plasma without added FXI set at 100% inhibition and those with plasma mixed with 25 nM FXI set as 0% inhibition.

MAbs that prolonged the aPTT as well as some control mAbs were purified, added to plasma and tested for effect on the aPTT, PT and FXI activity.

1.6 Thrombin Generation in Plasma

Thrombin generation in plasma in real time was measured as described by Hemker et al (Pathophysiol Haemost Thromb 2002; 32:249-53) and in the manual as provided by the manufacturer (Thrombinoscope, Maastricht, the Netherlands). Briefly, coagulation was triggered by recalcification of plasma either in the presence of 1 or 5 pM of recombinant human tissue factor (Innovin, Siemens Healthcare Diagnostics), or aPTT reagent (8 times diluted; Pathromtin SL, Siemens Healthcare Diagnostics), 4 µM phospholipids, and 417 µM fluorogenic substrate z-Gly-Gly-Arg-AMC (Bachem, Bubendorf, Switzerland). Fluorescence was monitored using a Fluoroskan Ascent Fluorometer (Thermolabsystems, Helsinki, Finland), and the endogenous thrombin potential (ETP), peak, time-to-peak, lag time and velocity index were calculated using Thrombinoscope® software.

1.7 Assays to Assess Effects of mAbs on Activation of FXI

Chromogenic assays were performed in 25 mM Hepes, pH 7.4, 137 mM NaCl, 3.5 mM KCl, 3 mM CaCl2 and 0.1 mg/ml bovine serum albumin (BSA).

To assess the effects of the anti-FXI mAbs on the activation of FXI by FXIIa, 100 nM purified FXI was incubated with 1 to 10-fold molar excess of mAb for 30 minutes at room temperature (RT). Next, 5 mM FXIIa was added and samples were incubated for 2 hours at RT. FXIa levels in the mixtures was then measured with chromogenic substrate S2366 (at 0.5 mM). This assay was performed with and without 50 nM high molecular weight kininogen (HK).

In a comparable experiment the effects of the anti-FXI mAbs on the activation of FXI by thrombin (FIIa) was evaluated. FXI (50 nM) was incubated with a 10-fold excess mAb for 30 minutes at RT. Then 10 nM thrombin was added and the mixtures were incubated overnight. The amount of FXIa generated in the mixtures was then measured by adding 1 U hirudin (to block thrombin) and the chromogenic substrate S2366 (0.5 mM).

1.8 Assays to Assess the Effects of mAbs on the Activity of FXIa

To assess the effects of purified anti-FXI mAbs on the enzymatic activity of FXIa, FXIa and purified mAb were incubated in chromogenic assay buffer, final concentrations 50 nM and 500 nM, respectively, for 30 minutes at 37° C. Then the chromogenic substrate S2366 was added at a final concentration of 0.5 mM and the conversion of the substrate was measured at 405 nm. In some experiments to confirm the effect of mAb anti-FXI 34.2 on the chromogenic activity of FXIa, slightly different conditions, i.e. 2.5 nM FXIa and 25 nM anti-FXI mAb were used.

To assess the effects of the anti-FXI mAbs on the activation of FIX by FXIa, 10 nM of FXIa was incubated with anti-FXI mAb in the chromogenic substrate buffer with 7 mM CaCl2 for 30 minutes at 37° C., then 100 nM FIX was added and the mixtures were incubated for 10 minutes at 37° C. To assess FIXa in the mixture, purified FX (100 nM) and the chromogenic substrate S2222 (0.5 mM) were added. The conversion of the chromogenic substrate was then measured at 405 nm.

1.9 Experimental Thrombosis Model in Mice

The animal procedures were performed at the Academic Medical Center (Amsterdam, The Netherlands) and approved by the Animal Care and Use Committee of the institute.

Eight-week-old male and female factor XI knock out-mice (FXI−/− mice) on C57BL/6 background were included in the present study (Rosen E D et al., Thromb Haemost 2002; 87:774-6). Mice were housed in micro-isolator cages on a constant light-dark cycle and were given access to food and water ad libitum.

Prior to the surgical procedure to induce thrombosis, the animals were supplemented with 5 U of human plasma factor XI concentrate (1 Unit is the amount of FXI present in 1 ml of pooled normal human plasma). Thereafter, the mice were intravenously injected with the mAb (8 mg/kg) or saline. Enoxaparin (LMWH; 1 mg/kg) was injected subcutaneously 6 hours before the procedure.

A well-established mouse thrombosis model, ferric chloride (FeCl3) induced inferior vena cava (IVC) thrombosis was used to evaluate the efficacy of the mAbs. Briefly, FXI−/− mice were anaesthetized with 2.5% inhalant isoflurane and a mixture of ketamin/xylazin (2:1). Then a midline incision was made and the IVC was exposed by blunt dissection. Subsequently, a filter paper soaked in a 10% FeCl3 solution was placed below the renal veins on the IVC for 3 minutes. The paper was removed and venous flow was measured for 30 to 45 minutes using a tissue perfusion monitor (type BLF22; Transonic Systems Inc. Ithaca, N.Y., USA). The flow before administration of FeCl3 was set at 100% and used as a reference. The flow rate after administration was calculated as % of this pre-administration flow. Groups of 6 mice were studied per treatment.

1.10 Bleeding Assay

A mouse tail bleeding assay was used as described (Wang X et al., J Thromb Haemost 2006; 4:1982-8). Briefly, mice were anaesthetized and placed on a 37° C. heating pad. At a tail diameter of about 1 mm (2-4 mm from the tip) the tail was cut and placed in filled saline at 37° C. Time until bleeding stopped was recorded. After 30 minutes the experiment was stopped even when the animals were still bleeding, and the animals were sacrificed. Blood loss was assessed by measuring the OD at 575 nM of the saline solution used to collect blood from the bleeding tail.

1.11 Cloning of cDNA of mAb Anti-FXI 34.2

Hybridoma cells were washed with PBS, aliquoted and stored as pellets at −80° C. RNA was isolated from these pellets by using RNeasy Mini Isolation Kit (QIAGEN). RNA concentration was determined with a spectrophotometer (A260 nm). By reverse transcriptase, cDNA was synthesized from 2 µg of RNA using the RevertAid™ H Minus First Strand cDNA Synthesis Kit (Fermentas) and stored at −20° C. until further use. Isotype-specific primers (sense and antisense) were designed to amplify the V-regions of the mouse mAb anti-FXI 34.2 (Table 1).

TABLE 1

PCR primers used to clone cDNA of mAb anti-FXI 34.2.

| | | SEQ ID NO |
|---|---|---|
| Heavy chain | | |
| sense | 5'-ATGGRATGGAGCKGGGTCTTTMTCTT-3' | 9 |
| antisense | 5'-CAGTGGATAGACAGATGGGGG-3' | 10 |
| Light chain | | |
| sense | 5'-ATGGGCWTCAAAGATGGAGTCACA-3' | 11 |
| antisense | 5'-ACTGGATGGTGGGAAGATGG-3' | 12 |

Degenerated primers:
M = C or A; R = A or G; and W = A or T.

To confirm the sequence of the V-regions of mAb anti-FXI 34.2 a chimeric human IgG4 format of mAb anti-FXI 34.2 was made in which the constant mouse k and CH domains were swapped for human domains. To ensure inter-heavy chain disulfide bridging a mutation in the hinge region was introduced in the sequence (S241P; Angal S et al., Mol Immunol 1992; 30:105-8). To this end, CHO cell-optimized cDNA sequences coding for chimeric human IgG4 heavy chain and for chimeric human K light chain were purchased from Geneart (Regensburg, Germany), which encoded for a murine signal peptide followed by either the murine variable heavy chain linked to the human IgG4 constant region or followed by the murine variable light chain linked to the human kappa constant region, respectively. The antibody was expressed in CHO cells using FreeStyle™ MAX CHO (CHO-S cells) Expression System (Invitrogen), purified with protein A affinity chromatography (GE Healthcare) and tested for binding to human FXI by ELISA in which human FXI was used as a coating, and for functional activity by adding protein G-purified preparations to human plasma and measuring the aPTT.

1.12 Human and Deimmunized Variant of Murine mAb Anti-FXI 34.2

The sequence of mouse mAb anti-FXI 34.2 was humanized and deimmunized using the Composite Human Antibody technology (www.antitope.co.uk). Composite human antibodies comprise multiple sequence segments ('composites') derived from V regions of unrelated human antibodies. All selected sequence segments derived from human V region databases were filtered in silico for the presence of potential T cell epitopes.

To this end, amino acids considered to be critical for antigen binding of the starting antibody were first determined. Then the sequences of VH and VK domains of mAb anti-FXI 34.2 were used to select homologous sequence segments derived from databases of unrelated human V regions. Four different VH and 4 different VK sequences were designed yielding 16 different antibodies. V region genes were then generated using synthetic oligonucleotides encoding combinations of selected human sequence segments. These were then cloned into vectors containing human IgG4 heavy chain containing the hinge stabilizing mutation S241P (Angal S et al., Mol Immunol 1992; 30:105-8) and kappa light chain. The chimeric antibody genes and all combinations of selected anti-FXI 34.2 IgG4 (S241P) were stably transfected into NSO cells via electroporation. The identity of each cell line was confirmed by DNA sequencing of the variable domains from genomic DNA. The best expressing lines were selected and used to express the 17 mAbs (16 Composite Human Antibody™ variants, and the mouse-human chimeric mAb anti-FXI 34.2). The recombinant antibodies were purified from cell culture supernatants on a Protein A Sepharose column (GE Healthcare).

To test the various mAbs for binding to human FXI, initially a competition ELISA was used, in which human FXI was used for coating, and biotinylated murine mAb anti-FXI 34.2 as reference antibody. To this end, a dilution series of purified murine mAb anti-FXI 34.2 antibody together with the chimeric antibody and each of the 16 composite variants of mAb anti-FXI 34.2 at concentrations of 16.66 µg/ml to 0.023 µg/ml were premixed with a constant concentration of biotinylated murine mAb anti-FXI 34.2 (0.12 jag/ml, final concentration) before incubating for 1 hour at room temperature on a Nunc Immuno MaxiSorp 96 well flat bottom microtitre plate pre-coated with 0.5 µg/ml Factor XI diluted in 1×PBS pH 7.4. The binding of the biotinylated antibody was detected with streptavidin-HRP (Sigma) and OPD substrate (Sigma. The reaction was stopped with 3M HCl, absorbance read at 490 nm on a Dynex Technologies MRX TC II plate reader and the binding curves plotted.

1.13 In Vitro Model to Evaluate Immunogenicity of Humanized mAb 34.2

The immunogenicity potential of the lead fully human composite lead anti-FXI mAb was assessed in vitro using peripheral blood mononuclear cells of HLA typed donors (EpiScreen™ technology; Antitope, Cambridge, UK). Briefly, peripheral blood mononuclear cells (PBMC) were isolated from healthy community donor buffy coats using Lymphoprep (Axis-shield, Dundee, UK) density centrifugation followed by T cell depletion (CD8+RosetteSep™; StemCell Technologies Inc, London, UK). Donors were typed for HLA-DR haplotypes using an HLA SSP-PCR based tissue-typing kit (Biotest, Solihull, UK). PBMC from 20 donors representing the number and frequency of HLA-DR allotypes expressed in the world and European/North American populations were selected and incubated with purified composite antibody at a final concentration of 50 µg/ml per sample. For each donor, a reproducibility control (cells incubated with 100 µg/ml Keyhole Limpet Haemocyanin (KLH), Pierce (Perbio), Cramlington, UK KLH), a clinical control (50 µg/ml humanised A33 antibody), a culture medium only control, and a control of the chimeric mouse-human mAb anti-FXI 34.2 were also included. Cultures were incubated for a total of 8 days. On days 5, 6, 7 and 8 proliferation of cells were measured by pulsing 3×100 µl aliquots in round bottomed 96 well plates with 0.75 µCi [3H]-Thymidine (Perkin ElmerR, Beaconsfield, UK) for a further 18 hours. Cells were then harvested onto filter mats (Perkin ElmerR) and counts per minute (cpm) for each sample were determined by Meltilex™ (Perkin ElmerR) scintillation counting. Stimulation indexes (SI) were then determined by assessing the ratio of proliferation (cpm) of PBMC incubated with test sample and that of PBMC incubated with medium only. A stimulation index ≥2 were considered to represent a significant response.

2. Results 2.1 Generation of Inhibitory Antibodies Against Human FXI

Figure 1B:
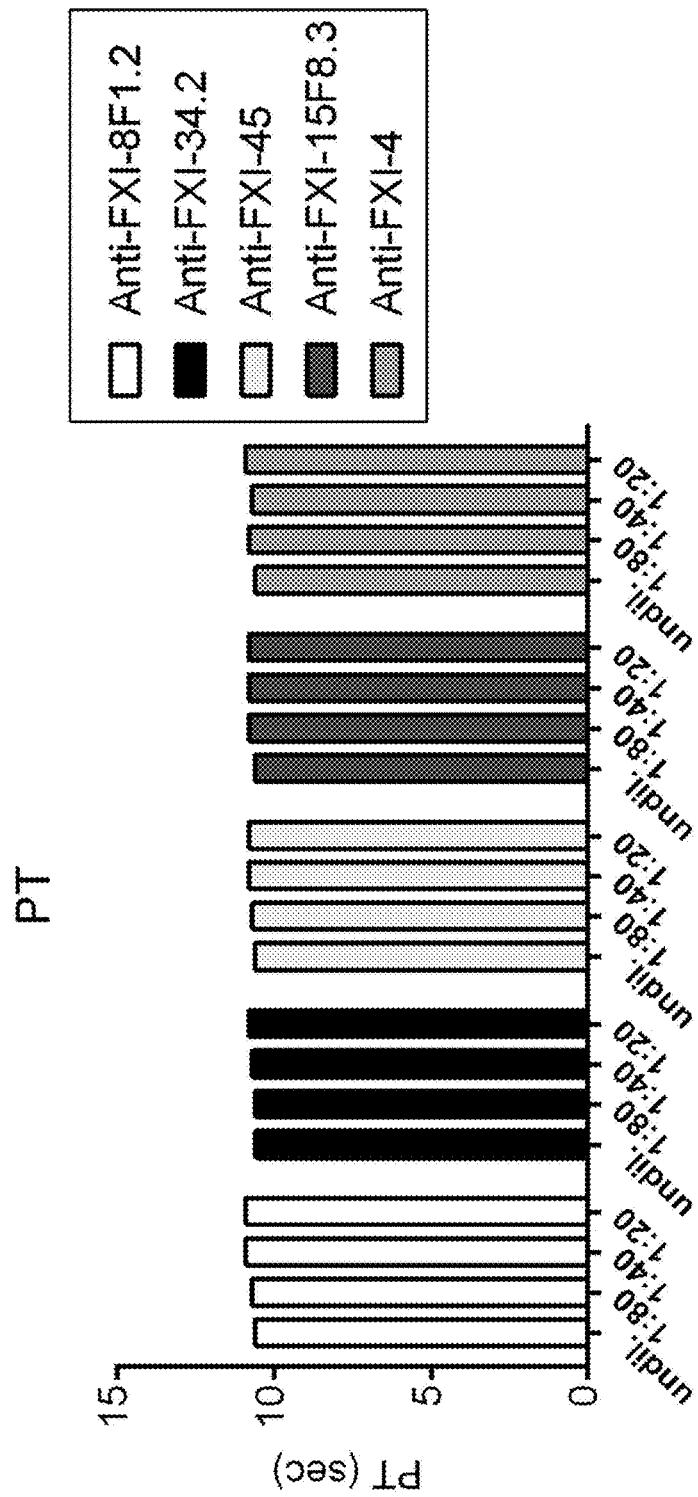
FIG. 1. Effect of purified mouse anti-human FXI mAbs on A) aPTT, B) PT or C) FXI activity of human plasma. MAbs at 0.2-0.9 mg/ml were diluted as indicated and mixed 1 to 1 with human plasma. APTT (A), PT (B) or C) FXI activity of the mixtures was measured.

Thirty-two hybridomas producing mAbs that bound to human FXI in the ELISA were generated. Supernatants of these hybridomas were added to human plasma and tested for inhibitory activity in the aPTT. In this aPTT FXI-deficient plasma supplemented with various amounts of FXI was used as reference. Two hybridoma supernatants, anti-FXI mAb 34.2 and anti-FXI mAb 15F8.3, inhibited FXI by more than 90%. These mAbs were subcloned by limited dilution and purified from hybridoma supernatant by Protein G affinity chromatography. Purified mAbs were added to human plasma and tested for effect on aPTT and PT clotting activity (FIGS. 1A and 1B). MAbs 34.2 and 15F8.3 dose-dependently prolonged the aPTT whereas they did not affect the PT. Moreover, control (non-inhibitory anti-FXI) mAbs had no effect in the aPTT test.

Figure 1C:
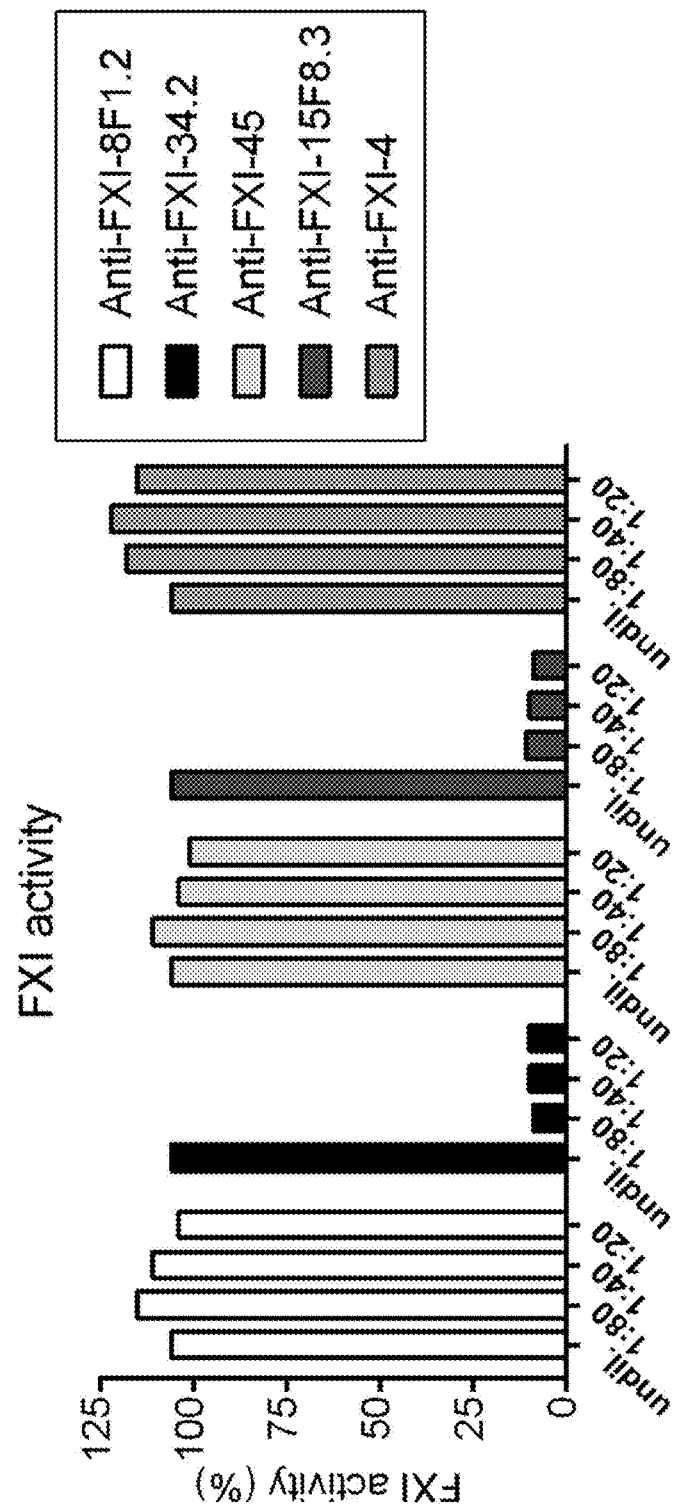

Finally, the mixtures of purified mAbs and human plasma were tested in a FXI clotting assay (FIG. 1C). The results were expressed as % FXI activity by reference to dilutions of a human plasma pool, which was said to contain 100% FXI. The two mAbs that prolonged the aPTT, reduced FXI activity in human plasma by >90%, whereas the other antibodies had no effect (FIG. 1C). Using Plasmon surface resonance (Biacore) the $K_D$ of mAb 34.2 for human FXI was found to be 0.2 nM, whereas that of mAb 15F8.3 was 0.15 nM.

2.2 Epitope Mapping

Figure 2A:
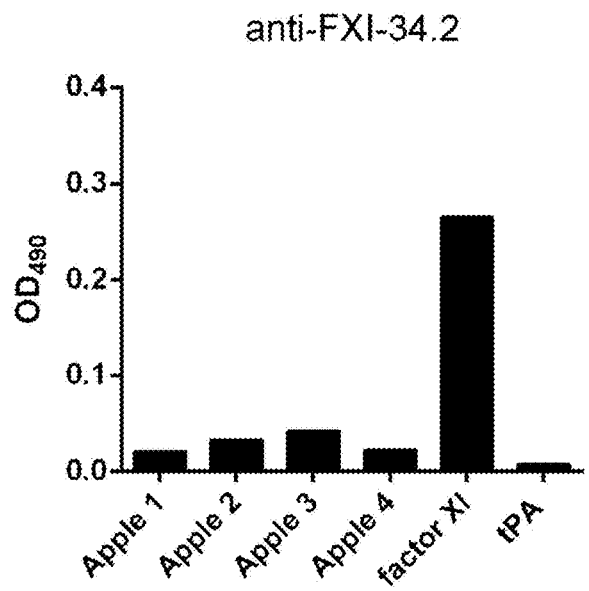
FIG. 2. MAb anti-FXI 34.2 binds to an epitope in the serine protease domain of FXI, and mAb anti-FXI 15F8.3 to an epitope in the apple 2 domain. ELISA wells were coated with fusion proteins of tPA and a single apple domain of FXI (indicated as Apple 1 to 4 in the Figure), or with purified plasma FXI (factor XI). Binding of anti-FXI mAb was detected with peroxidase-conjugated anti-mouse IgG antibodies. MAb anti-FXI 34.2 does not bind to any of the apple domains, but only to plasma factor XI which, in addition to 4 apple domains, also comprises the serine-protease domain.
Figure 2B:
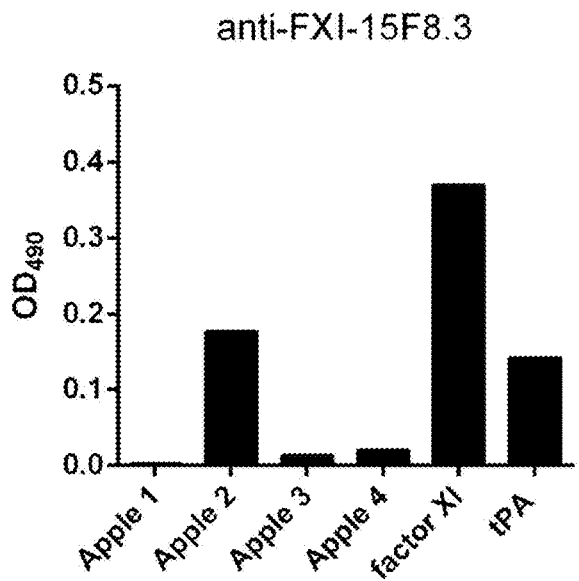

To map their epitopes on the domains of FXI, the mAbs were incubated in ELISA wells coated with recombinant fusion proteins of single apple domains with tPA, or with plasma FXI. Binding of the mAbs to the ELISA plate was assessed with peroxidase-conjugated anti-mouse IgG. Using this system, the epitope for mAb anti-FXI 15F8.3 was found to be located in the apple 2 domain, whereas mAb anti-FXI 34.2 did not bind to any of the apple domains and only bound to plasma FXI, suggesting its epitope to be located in the serine protease domain of FXI (FIG. 2).

2.3 Effects of Inhibitory Anti-FXI mAbs on Thrombin Generation in Plasma

Figure 3A:
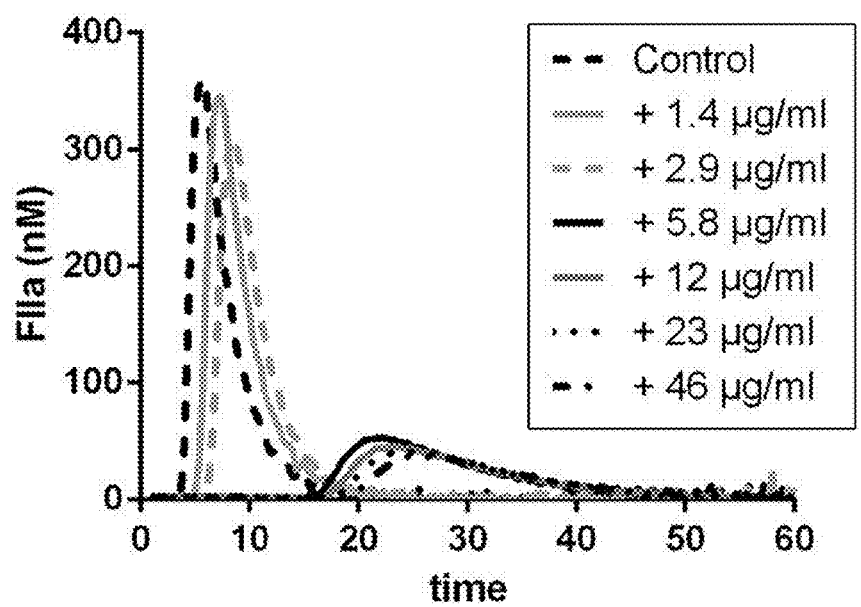
FIG. 3. Effect of mAb anti-FXI 34.2 on thrombin generation in plasma induced by A) aPTT reagent, B) low conc. TF (1 pM) or C) high conc. TF (5 pM). The mAb was added to pooled normal human plasma to a final concentration as indicated. aPTT reagent (A), TF at a final conc. of 1 pM (B) or TF at a final conc. of 5 pM (C) was added and the generation of thrombin was measured in real time as described in the Materials and Methods. X-axis represent time (minutes), Y-axis is thrombin (FIIa) concentration in plasma at the indicated time (nM).
Figure 3B:
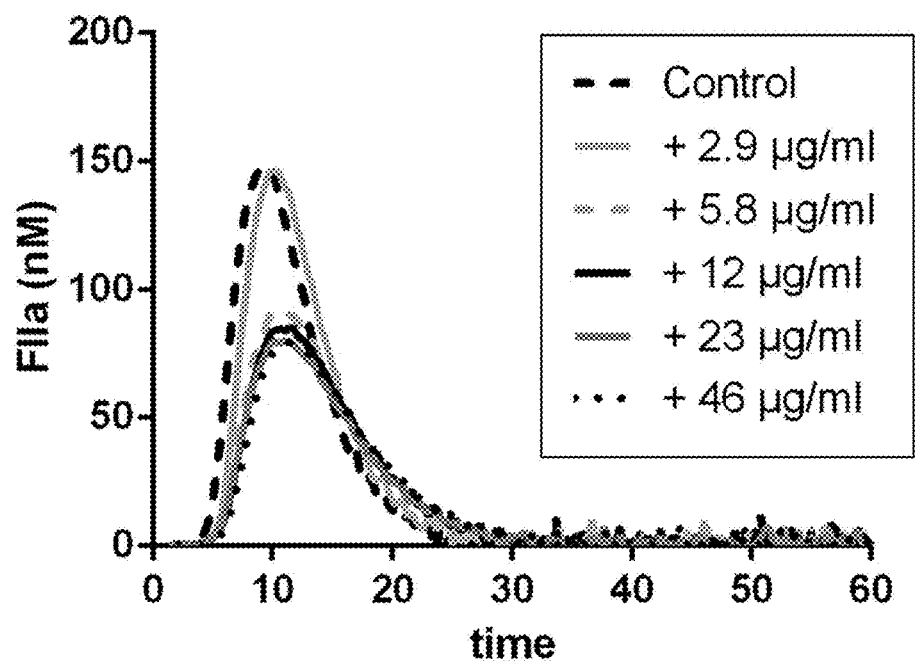
Figure 3C:
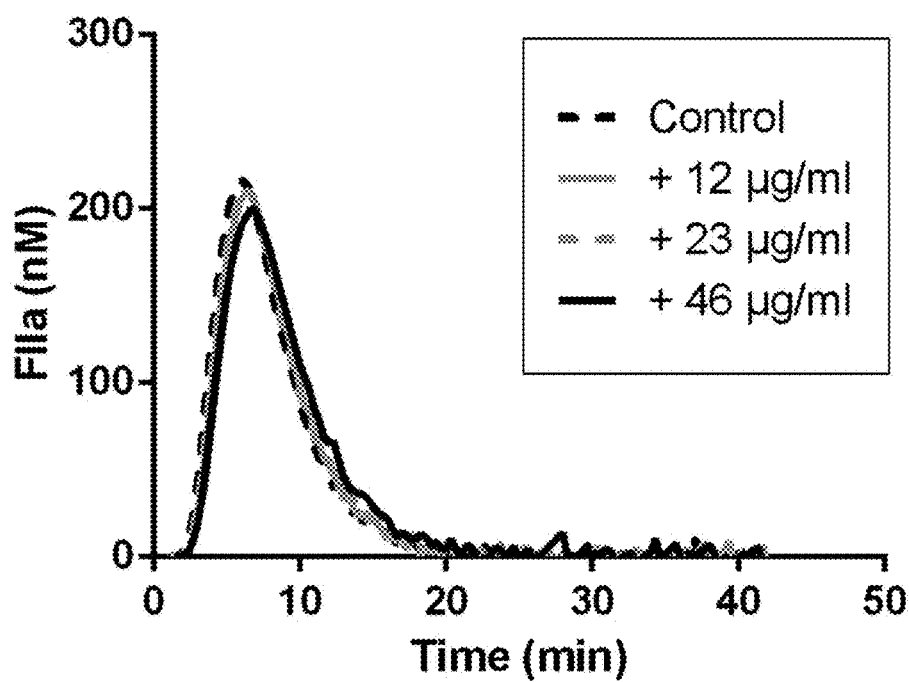

To assess the effects of the anti-FXI mAbs on FXI activity further, thrombin was generated in human plasma by various stimuli, high tissue factor (TF; 5 pM), low TF (1 pM) or aPTT reagent, in absence or presence of the anti-FXI mAbs, and measured in real time. The mAbs anti-FXI 34.2 (FIG. 3A) and anti-FXI 15F8.3 (data not shown) dose-dependently reduced thrombin generation induced by aPTT reagent, which is expected as they both prolong the aPTT when added to human plasma (see FIG. 1A). Thrombin generation in plasma induced by low TF concentration is known to be partly dependent on FXI. When thrombin generation was induced in plasma by low TF, only mAb anti-FXI 34.2 dose-dependently reduced thrombin by up to 30-40% (FIG. 3B). In contrast mAb 15F8.3 did not reduce thrombin generation by low TF (data not shown). Neither mAb anti-FXI 34.2 (FIG. 3C) nor mAb anti-FXI 15F8.3 (data not shown) had an effect on thrombin generation by high TF.

From these experiments it is concluded that mAb anti-FXI 34.2 inhibits FXI independently of the mechanism of activation whereas mAb anti-FXI 15F8.3 only inhibits FXI when activated by FXIIa. Therefore, mAb anti-FXI 34.2 was selected for further characterization and humanization.

2.4 Monoclonal Antibody Anti-FXI 34.2 Inhibits FXI Activity by Binding to the Active Site of FXI and Preventing FIX Activation A mAb against the active site of FXI/FXIa typically inhibits the conversion of substrates of FXIa including that of small substrates such as a chromogenic substrate. Large substrates such as FIX also interact with sites, known as exosites, on FXIa outside the active site, whereas small substrates exclusively interact with the active site only. Inhibition of the chromogenic activity of FXIa by a mAb therefore reveals that the epitope for that mAb is (at least partially) overlapping with the active site. Antibodies against exocytes are characterized by that they inhibit the conversion of large substrates by FXIa but have no effect on the chromogenic activity of FXIa. MAb anti-FXI 34.2 binds to the serine protease domain (FIG. 2), and inhibits the functional activity of FXI in plasma (FIG. 1C). Next this mAb was tested for its effects on the conversion of small substrates by FXIa. Purified factor XIa was incubated with mAb anti-FXI 34.2 as well as with control mAbs. Remaining FXIa activity was then measured with chromogenic substrate S2366.

Figure 4A:
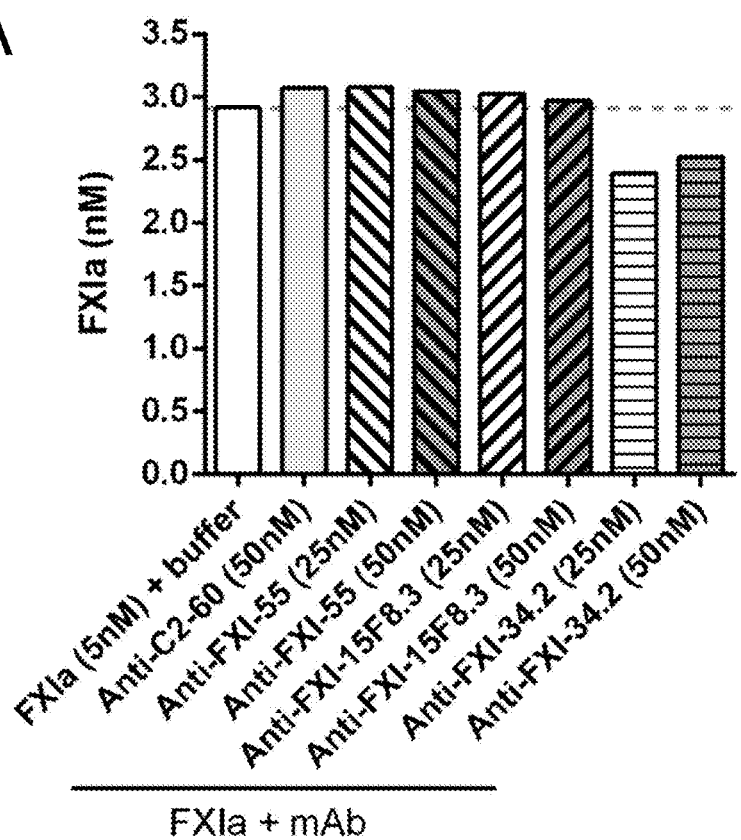
FIG. 4.

MAb anti-FXI-34.2 had a small inhibitory effect whereas none of the other mAbs inhibited FXIa chromogenic activity (FIG. 4A). This small effect of mAb anti-FXI 34.2 was consistently observed throughout the experiments and was also observed in another experiment with a recombinant chimeric human-mouse mAb format of anti-FXI 34.2. As the chromogenic substrate S2366 consists of a small tripeptide linked to p-Nitroaniline (L-Pyroglutamyl-L-prolyl-L-arginine-p-Nitroaniline), the inhibitory effect of mAb anti-FXI 34.2 reveals that it binds to an epitope (at least partially) overlapping the active site of FXIa. It is to be noted that mAb anti-FXI 34.2 has a high affinity to non-activated FXI (apparent $K_D$ with surface plasmon resonance of 0.2 nM; see result section 2.1) and therefore the epitope of mAb anti-FXI 34.2 is expressed on FXI as well as on FXIa.

Figure 4B:
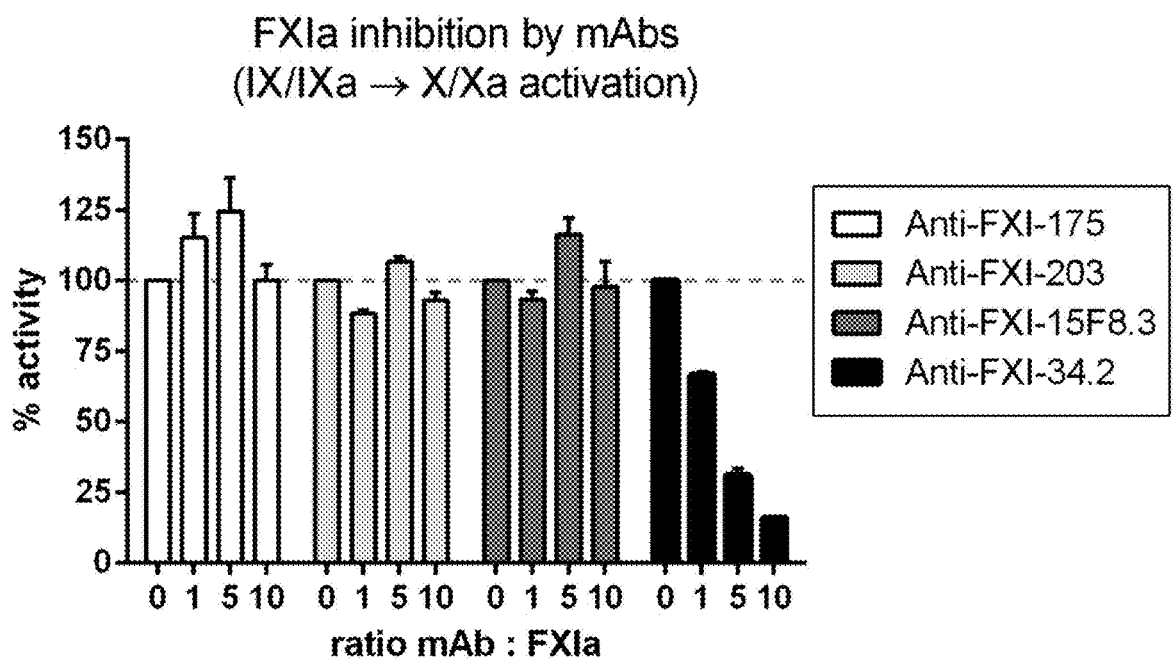

Chromogenic substrates are relatively small, whereas the natural substrate of FXIa, clotting factor IX (FIX), is a relatively large substrate. In another set of experiments the activity of FXIa was measured by monitoring the conversion of FIX into FIXa. FIXa activity was measured with FX as substrate, which is converted into FXa, which then is measured with chromogenic substrate S2222. MAb anti-FXI 34.2 inhibits the conversion of FIX into FIXa by FXIa, whereas control mAbs had no effect (FIG. 4B).

Thus the experiments shown in this example indicate that mAb FXI 34.2 inhibits FXI activity by inhibiting the conversion of substrates of FXIa by binding to an epitope (at least partially) located in the active site. This mechanism of action of mAb anti-FXI 34.2 is unique and has not been described before for an antibody against human FXI.

2.5 Effects of mAb Anti-FXI 34.2 in a Mouse Model for Experimental Thrombosis

Figure 5A:
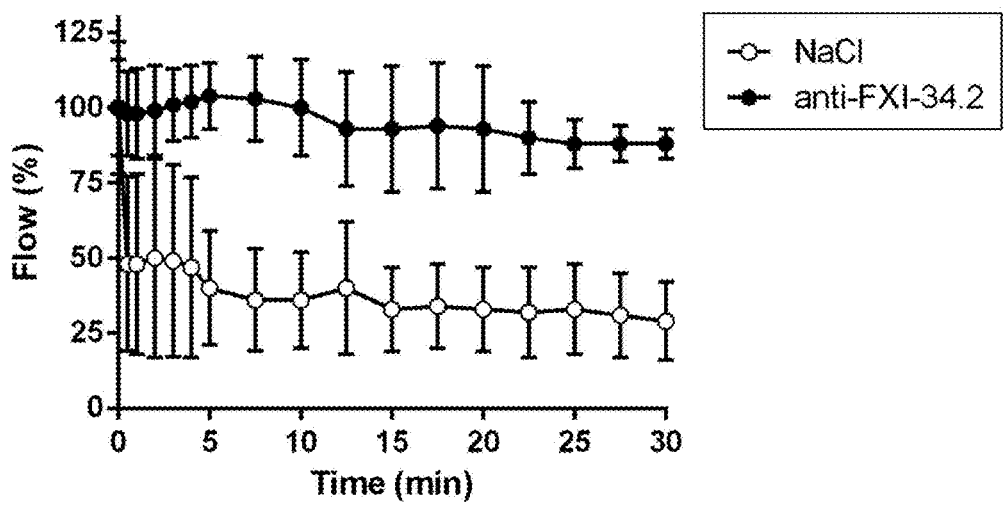

The mouse model for inferior vena cava (IVC) thrombosis in FXI-knock-out mice (Wang X et., J Thromb Haemost 2006; 4:1982-8) supplemented with human FXI (van Montfoort M et al., Thromb Haemost 2013; 110:1065-73) was used to evaluate the effects of mAb anti-FXI 34.2. Without exogenous FXI the aPTT in the FXI–/–-mice is >150 sec versus 25-34 sec in wild-type mice. IVC thrombosis was induced by application of 10% FeCl3 to the IVC. A rapid decline of the blood flow through the IVC was observed within 1 minute following 10% FeCl3 application (saline group in FIG. 5A). Enoxaparin treatment of the mice completely prevented this FeCl3 induced blood flow impairment during the observation period of 45 minutes (van Montfoort M et al., Thromb Haemost 2013; 110:1065-73; see FIG. 7 of this article). Administration of mAb anti-FXI 34.2 before induction of thrombosis with ferric chloride prevented blood flow impairment throughout the whole observation period (FIG. 5A).

Figure 5B:
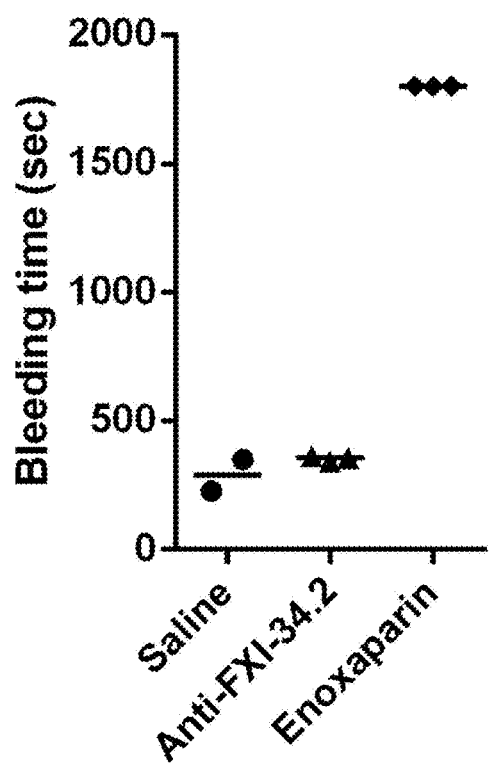

To evaluate the impact of mAb anti-FXI 34.2 on normal hemostasis a tail bleeding assay (Wang X et., J Thromb Haemost 2006; 4:1982-8) was used. MAb anti-FXI 34.2 had no effect on tail bleeding time, in contrast to Enoxaparin that markedly prolonged the time of tail bleeding (FIG. 5B). In contrast, Enoxaparin treated animals bled until the end of the observation time (30 minutes).

Thus, the experiments described in this example demonstrate that mAb anti-FXI 34.2 is as effective as enoxaparin to prevent thrombosis, but in contrast to enoxaparin, mAb anti-FXI 34.2 does not affect the bleeding time.

2.6 cDNA Sequence of mAb Anti-FXI 34.2

VH and Vκ regions of mAb anti-FXI 34.2 were cloned as described in method section above. The amino acid sequences of the VH and Vκ domains of mAb anti-FXI 34.2 are presented in the sequence listing as SEQ ID NO.'s 1 and 2, respectively. These sequences were used to construct a chimeric mAb with mouse VH and Vκ variable domains linked to CH domains of human IgG4 and human Cκ domains.

Figure 6A:
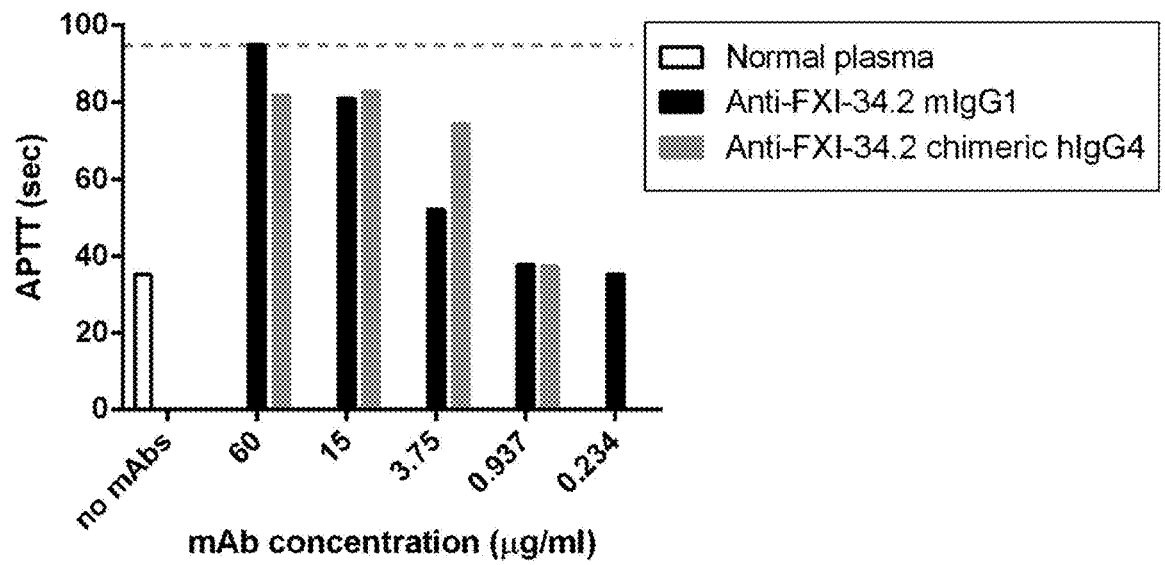
Figure 6B:
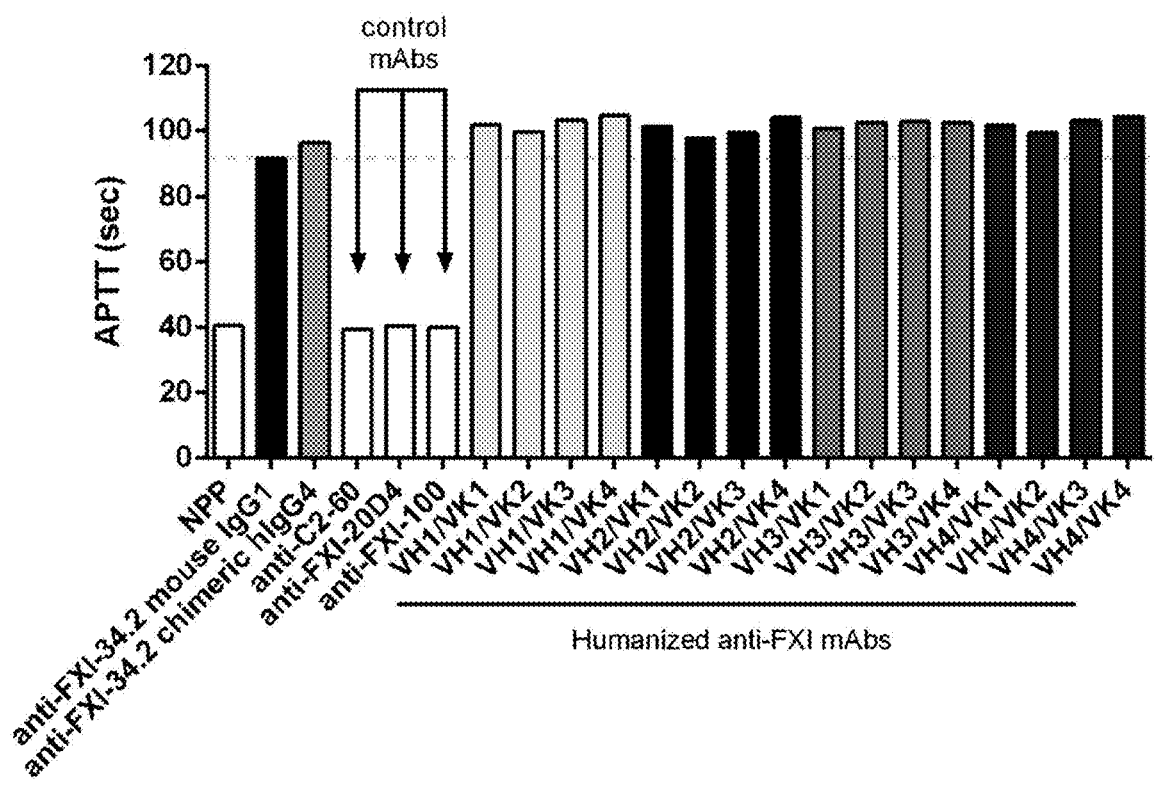

The mouse-human chimeric mAb anti-FXI 34.2 was expressed in CHO cells, purified and tested for inhibitory activity by mixing it with normal plasma and measuring the aPTT of the mixtures (FIG. 6A). As shown in FIG. 6A, the mAb anti-FXI 34.2 and the mouse-human chimeric mAb anti-FXI 34.2 dose-dependently reduced the aPTT(s).

2.7. Humanization of mAb anti-FXI 34.2

Based on the sequences of mAb anti-FXI composite human anti-FXI mAbs with minimal, if any, immunogenicity were designed using the Composite Human Antibody platform (Antitope, Cambridge, UK).

The VH and Vκ sequences of mAb anti-FXI 34.2 were found to consist of typical framework residues and CDR 1, 2 and 3 motifs as are shown in Table 3.

TABLE 3

Amino acid sequences of the CDRs (hyper variable regions) in the heavy and light chain variable domains of the mAb anti-FXI 34.2.

| CDR | Amino acid sequence | SEQ ID NO |
|---|---|---|
| HVR-H1 | RYWMH | 3 |
| HVR-H2 | NIYPDSDSTNYDEKFRT | 4 |
| HVR-H3 | MGFYAMDY | 5 |
| HVR-L1 | KASENVVTYVS | 6 |
| HVR-L2 | GASNRYT | 7 |
| HVR-L3 | GQSYSYPLT | 8 |

The protein sequence numbering is according to Kabat.

From the above analysis, it was considered that composite human sequences of mAb anti-FXI 34.2 could be created with many alternative residues outside of the CDRs but with only a few possible residues within the CDR sequences. Preliminary analysis indicated that corresponding sequence segments from several human antibodies could be combined to create CDRs similar or identical to those in the murine sequences. For regions outside of and flanking the CDRs, a wide selection of human sequence segments were identified as possible components of the novel composite human anti-FXI antibody V regions.

Based upon the structural analysis, a large preliminary set of sequence segments that could be used to create a humanized mAb anti-FXI 34.2 were selected and analysed in silico for presence of known antibody sequence-related T cell epitopes. Sequence segments that were identified as potentially immunogenic in humans were discarded. This resulted in a reduced set of segments. Combinations of these were again analysed for potential immunogenicity to ensure that the junctions between segments did not contain potential T cell epitopes. Selected sequence segments were assembled into complete V region sequences that were devoid of significant T cell epitopes. Four preferred heavy chain (VH1-4) and four light chain sequences (VK1-4) were then selected. Table 4 provides an overview of the SEQ ID NO.'s presenting the amino acid sequences of the four preferred heavy chain (VH1-4) and four light chain sequences (VK1-4).

TABLE 4

Sequences of 4 different variable regions of the heavy chain 1-4). (VH variant 1-4) and 4 of the light chain (Vκ variant

| Variable region | Amino acid SEQ ID NO | Nucleotide SEQ ID NO |
|---|---|---|
| 34.2 VH Variant 1 | 13 | 21 |
| 34.2 VH Variant 2 | 14 | 22 |
| 34.2 VH Variant 3 | 15 | 23 |
| 34.2 VH Variant 4 | 16 | 24 |
| 34.2 Vκ Variant 1 | 17 | 25 |
| 34.2 Vκ Variant 2 | 18 | 26 |
| 34.2 Vκ Variant 3 | 19 | 27 |
| 34.2 Vκ Variant 4 | 20 | 28 |

The protein sequence numbering is according to Kabat.

All variant Composite Human Antibody™ VH and Vκ region genes for mAb anti-FXI34.2 were synthesized and expressed with kappa light chain and IgG4 (S241P, hinge mutant; Angal S et al., Mol Immunol 1992; 30:105-8) heavy chain. Constructs were confirmed by sequencing. The VH and Vκ sequences of the original murine mAb anti-FXI 34.2 antibody were also expressed. The chimeric antibody genes and all possible combinations of composite mAb anti-FXI 34.2 IgG4 (S241P) VH and Vκ chains, i.e. a total of 16 pairings, VH1 combined with Vκ1, Vκ2, Vκ3 or Vκ4; VH2 with Vκ1, Vκ2, Vκ3 or Vκ4; and so on, were stably transfected into NSO cells via electroporation. The various composite human variants of mAb anti-FXI 34.2 are indicated further according to their chain composition, i.e. VH1Vκ1, VH2Vκ4 and so on. The best expressing lines were used to express the 17 mAbs (16 Composite Human Antibody™ variants, and the mouse-human chimeric mAb anti-FXI 34.2). The recombinant antibodies were purified from cell culture supernatants on a Protein A Sepharose column (GE Healthcare) and tested for binding to human FXI in a competition ELISA, as described in method section. The results revealed that all composite variants of mAb anti-FXI 34.2 bound equally well to human FXI as the mouse-human chimeric mAb anti-FXI 34.2 (data not shown).

The data were then used to calculate IC50 values for each antibody and these were normalised to the IC50 of the chimeric mouse-human mAb anti-FXI 34.2 antibody (Table 5). The normalised IC50 data for all variants tested are in the range of 0.69 to 1.13 indicating that the binding efficiencies of all composite anti-FXI mAbs were comparable to that of chimeric 34.2. Moreover, most variants were better expressed by the respective NSO cell-line than the chimeric antibody.

TABLE 5

Relative $IC_{50}$, $K_D$ and relative aPTT of the composite human mAbs derived from mAb anti-FXI 34.2

| Composite mAb | Relative $IC_{50}$[1] | APTT (% NPP) | $K_D$ (nM) |
|---|---|---|---|
| VH1/Vκ1 | 0.75 | 253 | 0.12 |
| VH1/Vκ2 | 0.69 | 248 | 0.25 |
| VH1/Vκ3 | 0.91 | 257 | 0.17 |
| VH1/Vκ4 | 0.89 | 260 | 0.35 |
| VH2/Vκ1 | 0.84 | 252 | 0.24 |
| VH2/Vκ2 | 0.92 | 243 | 0.88 |
| VH2/Vκ3 | 0.93 | 247 | 0.51 |
| VH2/Vκ4 | 0.98 | 259 | 0.062 |
| VH3/Vκ1 | 0.87 | 250 | 0.13 |
| VH3/Vκ2 | 0.87 | 255 | 0.079 |
| VH3/Vκ3 | 0.99 | 256 | 0.081 |
| VH3/Vκ4 | 1.13 | 255 | 0.42 |
| VH4/Vκ1 | 0.91 | 253 | 1.14 |
| VH4/Vκ2 | 0.76 | 247 | 0.071 |
| VH4/Vκ3 | 0.99 | 256 | 0.14 |

TABLE 5-continued

Relative IC$_{50}$, K$_D$ and relative aPTT of the composite human mAbs derived from mAb anti-FXI 34.2

| Composite mAb | Relative IC$_{50}$[1] | APTT (% NPP) | K$_D$ (nM) |
|---|---|---|---|
| VH4/Vκ4* | 1.09 | 259 | 0.13 |
| aC2-60 (control) | NA | 97 | NA |

[1]IC$_{50}$ value as determined in competition ELISA relative to IC$_{50}$ of mouse-human chimeric mAb anti-FXI 34.2;
*selected for further experiments To confirm the affinities of the composite human anti-FXI mAbs they were tested for binding to FXI with plasmon surface resonance using the Biacore system. Mouse mAb anti-FXI 34.2 has a K$_D$ of 0.2 nM for binding to FXI. Results are summarized in Table 5 above.

The affinities measured with the composite human mAbs ranged from 0.071 to 1.14 nM, (Table 5) indicating a slightly lower affinity for some and a slightly higher affinity for other anti-FXI composite mAbs, as compared to mouse mAb anti-FXI 34.2, which has a K$_D$ of 0.2 nM.

The inhibitory activity of the composite mAbs was assessed by mixing purified mAbs with normal human plasma and by measuring the aPTT of the plasma mixtures. The results indicated that all composite human anti-FXI mAbs prolonged the aPTT to a comparable extent (see FIG. 6B; Table 5).

These experiments revealed that all composite human anti-FXI antibodies had an affinity in the range of the original mouse mAb anti-FXI 34.2 which has a K$_D$ of 0.2 nM with the possible exception of the composite mAbs VH2Vκ3 and VH4Vκ1, which have a K$_D$ slightly above that of the mouse mAb. Regarding functional activity as measured in the aPTT all composite mAbs also had an inhibitory activity comparable to that of mouse mAb anti-FXI 34.2. Finally all mAbs had decent expression levels in NSO cells. The composite mAb VH4Vκ4 was predicted to have the lowest immunogenicity potential, and as this mAb was comparable to most other mAbs regarding affinity, functional activity and expression, this composite mAb VH4Vκ4 was selected for further analysis. Notably the format of this antibody is human IgG4 as for in vivo use it is not intended interact with complement or Fcγ-receptors. A mutation in the hinge region (S241P) was introduced in the IgG4 heavy chain as this mutation favors inter-chain disulfide bridging of the IgG4 heavy chains, rather than intra-chain disulfide bridge formation.

2.8 Immunogenicity Potential of mAb VH4Vκ4

Figure 7A:
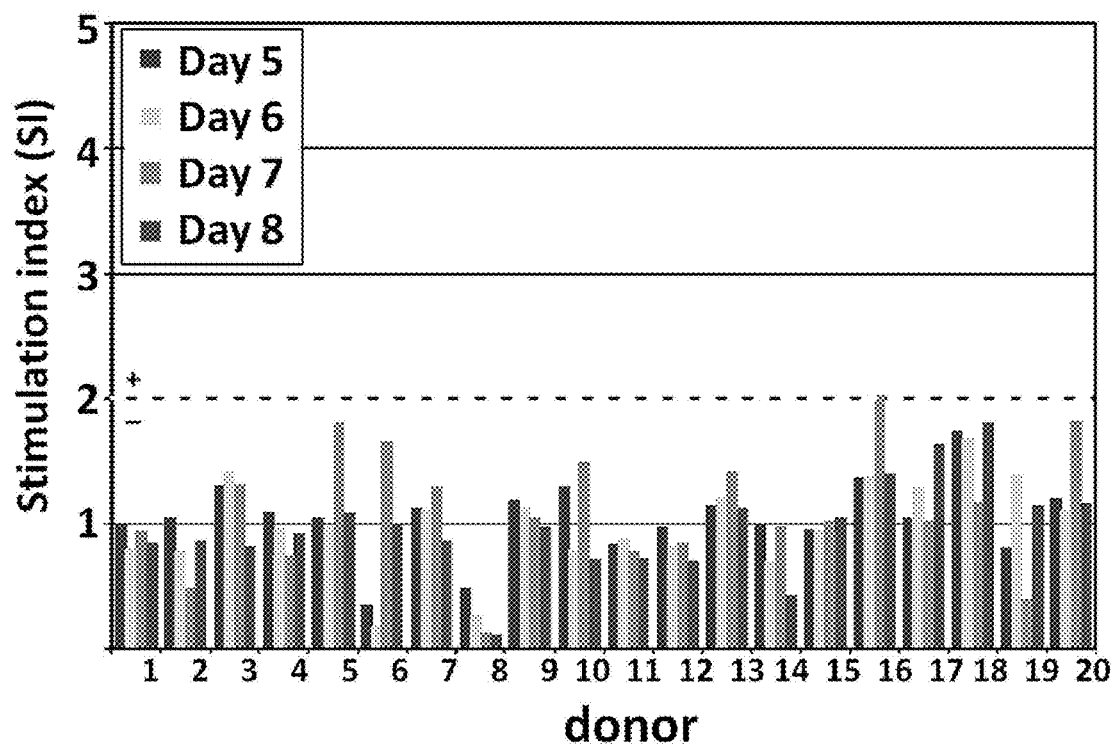
Figure 7B:
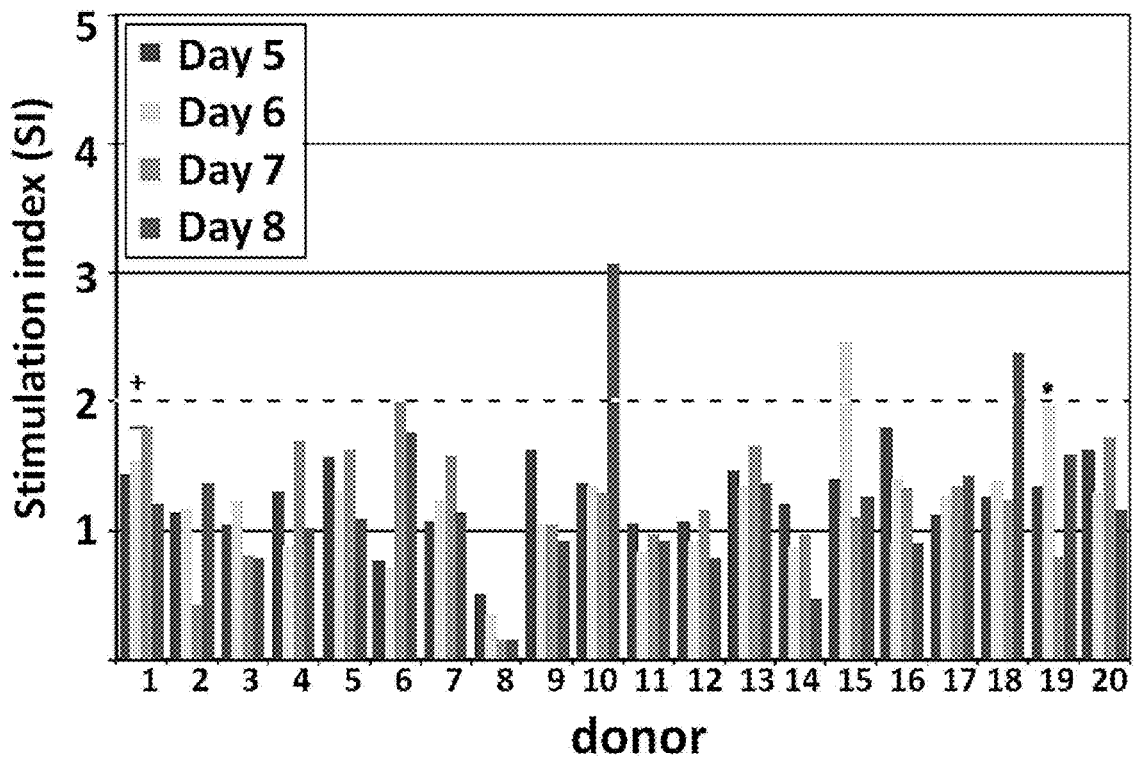

The immunogenicity potential of mAb VH4Vκ4 was tested by incubation with PBMC from a panel of 20 healthy donors and measuring the proliferation of the cells in time. In this test mAb VH4Vκ4 is tested at a final concentration of 50 μg/ml. To further improve the assay four daily measurements of proliferation as a measure for T cell activation was assessed at days 5 to 8. MAb VH4Vκ4 did not affect PBMC viability as was determined with cells from 6 donors and trypan blue dye exclusion of PBMC after 7 days culture (FIG. 7A). In addition, FIG. 7B gives the proliferation results observed with the mouse-human chimeric mAb anti-FXI 34.2. As can be seen, with PBMCs from 4 donors significant proliferation was observed and with PBMC from another donor borderline proliferation occurred.

In general stimulation indices observed with mAb VH4Vκ4 were lower than those observed with the chimeric mAb anti-FXI 34.2, on only one occasion a SI just above 2 was observed. These data indicate less proliferation of CD4 T cells upon incubation with mAb VH4Vκ4 than with the chimeric mAb. Thus, these results supported the lower immunogenicity potential mAb VH4Vκ4 as compared to the mouse-human chimeric mAb anti-FXI 34.2.

2.9 In Vitro Testing of mAb VH4Vκ4

Figure 8A:
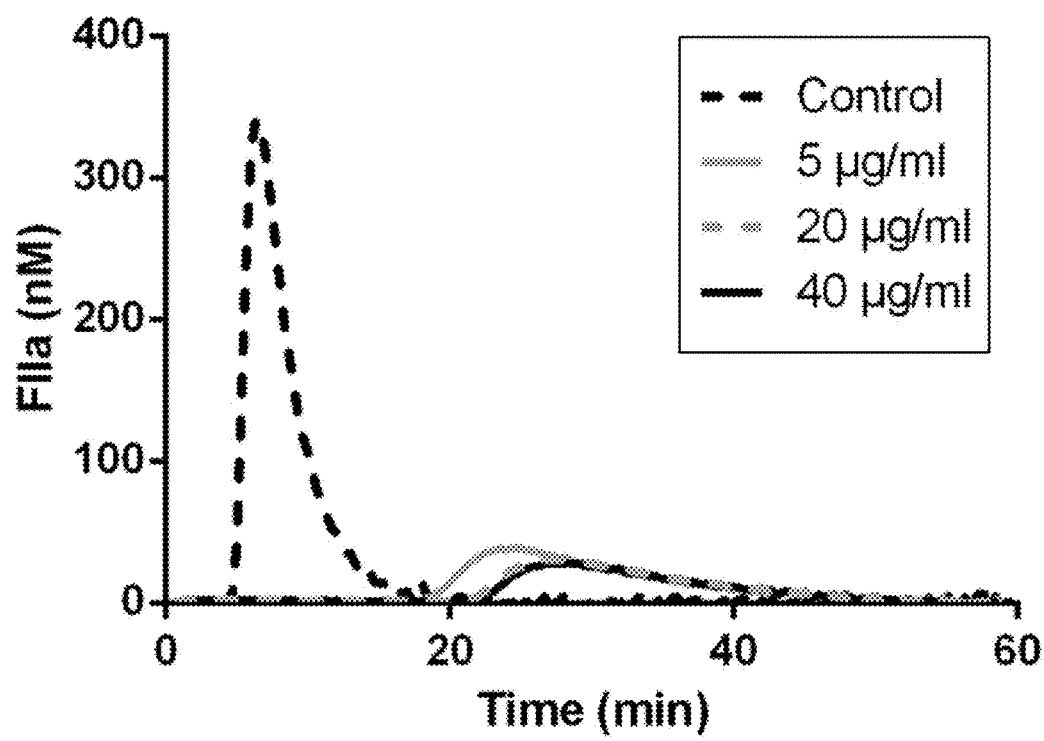
Figure 8B:
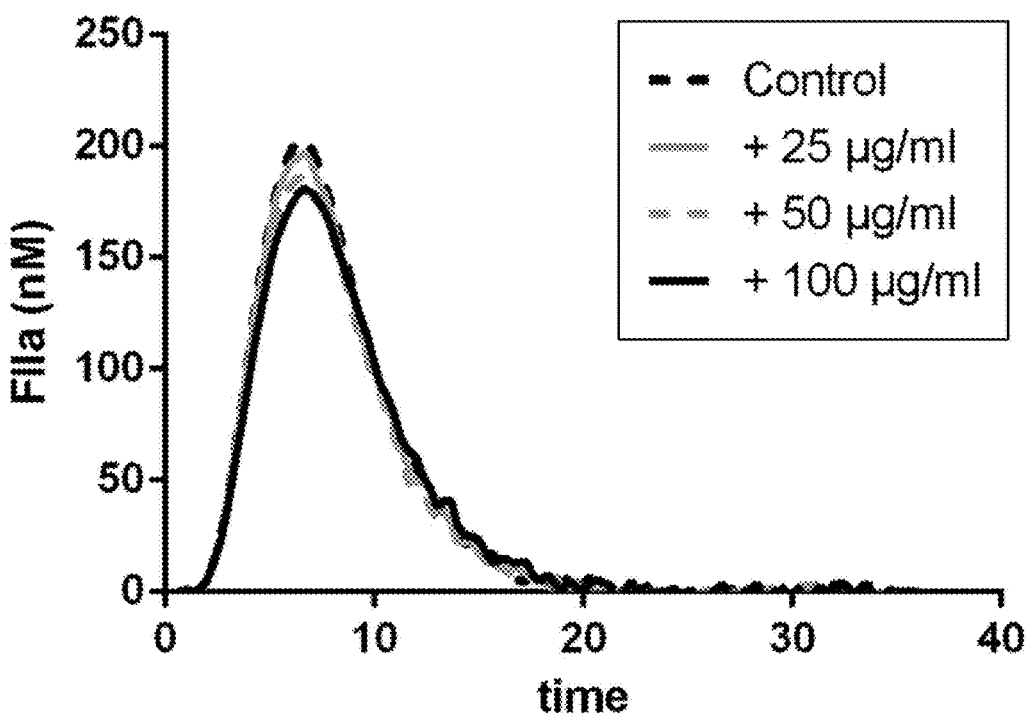
Figure 8C:
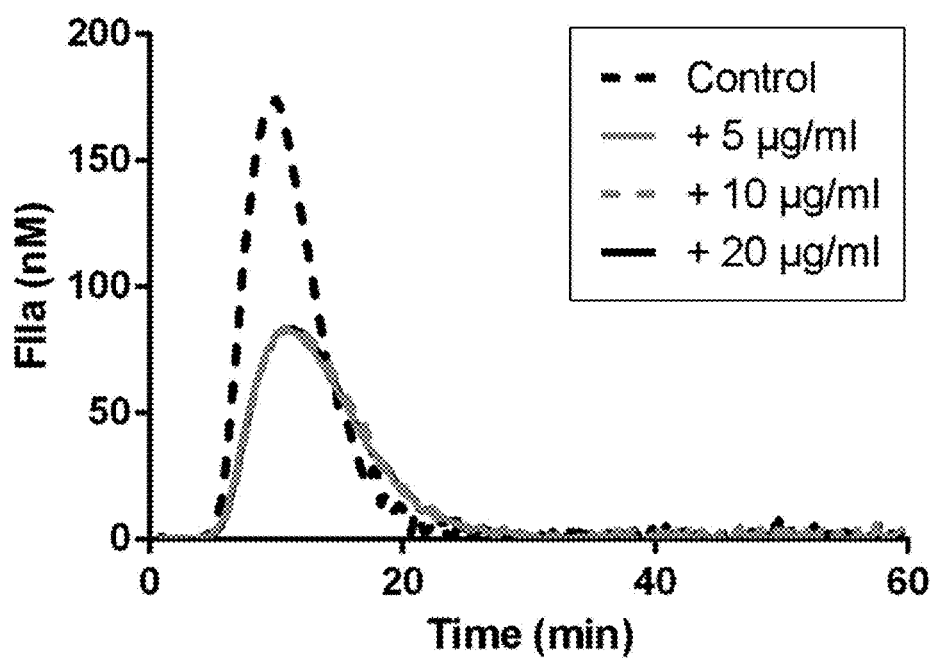

Addition of purified mAb VH4Vκ4 to human plasma virtually abolished thrombin generation induced by aPTT reagent (FIG. 8A), whereas the effect on thrombin generation by TF was dependent on the dose of TF used to generate thrombin in plasma (FIG. 8B-D). MAb VH4Vκ4 thus showed in these experiments the typical behaviour of a FXI inhibitor, which is complete inhibition of thrombin generation induced by aPTT reagent, partial inhibition of thrombin generation by low TF concentration and no inhibition of thrombin generation at high TF concentrations.

2.10 In Vivo Testing of mAb VH4Vκ4 in a Mouse Model for Thrombosis

MAb VH4Vκ4 was tested in vivo in the mouse model for thrombosis as described in section 2.5. Administration of the humanized mAb VH4Vκ4 before induction of thrombosis with FeCl3 prevented blood flow impairment during the whole observation indicating MAB VH4Vκ4 effectively prevented the formation of thrombosis (FIG. 9).

The invention claimed is:

1. A humanized antibody or an antigen-binding fragment thereof, that binds the light chain of factor XI (FXI) and reduces the chromogenic activity of activated factor XI (FXIa) on L-pyroglutamyl-L-prolyl-L-arginine-p-nitroaniline, wherein the heavy chain variable domain of the antibody comprises an amino acid sequence with at least 95% sequence identity to at least one of SEQ ID NO's: 13-16, and wherein the light chain variable domain of the antibody comprises an amino acid sequence with at least 95% sequence identity to at least one of SEQ ID NO's: 17-20 wherein the antibody or an antigen-binding fragment thereof comprises the hypervariable regions (HVR): HVR-H1 comprising the sequence of SEQ ID NO: 3, HVR-H2 comprising the sequence of SEQ ID NO: 4, HVR-H3 comprising the sequence of SEQ ID NO: 5, HVR-L1 comprising the sequence of SEQ ID NO: 6, HVR-L2 comprising the sequence of SEQ ID NO: 7 and HVR-L3 comprising the sequence of SEQ ID NO: 8.

2. The humanized antibody or the antigen-binding fragment of claim 1, wherein the antibody or antibody fragment has a $K_D$ for FXI of <1 nM.

3. The humanized antibody or the antigen-binding fragment of claim 2, wherein the antibody or antibody fragment has a $K_D$ for FXI of <0.2 nM.

4. The humanized antibody or the antigen-binding fragment of claim 1, wherein the heavy chain variable domain of the antibody comprises the amino acid sequence of SEQ ID NO: 16 and the light chain variable domain of the antibody comprises the amino acid sequence of SEQ ID NO: 20.

5. The humanized antibody or the antigen-binding fragment of claim 1, wherein the antibody or antibody fragment comprises a mutation in the hinge region that favors inter-chain disulfide bridging of the heavy chains over intra-chain disulfide bridge formation.

6. The humanized antibody or the antigen-binding fragment of claim 5, wherein the mutation is S241P.

7. The humanized antibody or the antigen-binding fragment of claim 1, wherein the antibody comprises a heavy chain constant region that is an IgG4 region.

8. The humanized antibody or the antigen-binding fragment of claim 1, wherein the antibody binds the light chain of human FXIa.

9. A pharmaceutical composition comprising the humanized antibody or the antigen-binding fragment of claim 1.

10. The pharmaceutical composition of claim 9, wherein the composition further comprises a pharmaceutically acceptable carrier.

11. A method for treating at least one of:
  i) a disease, disorder or condition that is mediated by FXI activation; and
  ii) a disease, disorder or condition wherein inhibition of FXI has a beneficial effect, wherein the method comprises administering in a subject in need thereof an effective amount of the humanized antibody or the antigen-binding fragment according to claim 1
and wherein the method is for the treatment of a pathological thrombosis or for reducing the risk of thrombosis in a subject who is at increased risk of developing thrombosis due to a medical procedure.

12. The method of claim 11, wherein the disease, disorder or condition is a thrombo-embolic disease.

13. The method of claim 11, wherein the antibody or the antigen-binding fragment is administered intravenously intra-arterially, intramuscularly or subcutaneously.

14. The method of claim 13, wherein the antibody or the antigen-binding fragment is administered intravenously as a bolus infusion or as a continuous infusion over a period of from less than 2 hours to 24 hours.

* * * * *